United States Patent
Yates et al.

(10) Patent No.: US 11,567,074 B2
(45) Date of Patent: Jan. 31, 2023

(54) METHODS FOR IDENTIFYING PROTEINS THAT BIND LIGANDS

(71) Applicant: University of Pittsburgh—Of the Commonwealth System of Higher Education, Pittsburgh, PA (US)

(72) Inventors: Nathan A. Yates, Piscataway, NJ (US); Steven James Mullett, McMurray, PA (US); Harris B. Bell-Temin, Gibsonia, PA (US); Andrey Bondarenko, Pittsburgh, PA (US)

(73) Assignee: University of Pittsburgh—Of the Commonwealth System of Higher Education, Pittsburgh, PA (US)

( * ) Notice: Subject to any disclaimer, the term of this patent is extended or adjusted under 35 U.S.C. 154(b) by 723 days.

(21) Appl. No.: 16/336,079

(22) PCT Filed: Sep. 25, 2017

(86) PCT No.: PCT/US2017/053207
§ 371 (c)(1),
(2) Date: Mar. 22, 2019

(87) PCT Pub. No.: WO2018/058023
PCT Pub. Date: Mar. 29, 2018

(65) Prior Publication Data
US 2019/0227062 A1    Jul. 25, 2019

Related U.S. Application Data

(60) Provisional application No. 62/399,777, filed on Sep. 26, 2016.

(51) Int. Cl.
*G01N 33/566*    (2006.01)
*G01N 33/68*    (2006.01)
(Continued)

(52) U.S. Cl.
CPC ........... *G01N 33/566* (2013.01); *G01N 33/53* (2013.01); *G01N 33/68* (2013.01); *G01N 33/94* (2013.01);
(Continued)

(58) Field of Classification Search
CPC ...... G01N 33/566; G01N 33/53; G01N 33/68; G01N 33/94; G01N 2030/8831; G16B 20/00
See application file for complete search history.

(56) References Cited

U.S. PATENT DOCUMENTS 5,462,863 A * 10/1995 Hsieh ................... C07K 14/005
530/421
6,906,320 B2    6/2005 Sachs et al.
(Continued)

OTHER PUBLICATIONS

Steketee, "Investigating the mod of action of AN5568, a novel therapeutic against African trypanosomiasis," PhD dissertation, University of Glasgow, <https://theses.gla.ac.uk/7478/1/2016steketeephd.pdf>, Mar. 2016. (Year: 2016).*
(Continued)

*Primary Examiner* — Jennifer Wecker
*Assistant Examiner* — Michael Paul Shimek
(74) *Attorney, Agent, or Firm* — Foley & Lardner LLP

(57) ABSTRACT

Provided herein are methods of identifying a protein capable of binding a ligand, the method comprising: (a) contacting the ligand with two or more samples comprising a plurality of proteins in a solution; (b) separating the proteins bound to the ligand ("bound proteins") from the proteins that are not bound to the ligand ("unbound proteins") in each sample; (c) denaturing and digesting the bound proteins to form a plurality of peptides in each sample; (d) quantifying a plurality of molecular features contained in the plurality of peptides in each sample, wherein the molecular features are defined as having a mass to charge ratio, retention time, and
(Continued)

peak intensity as measured by mass spectrometry; and (e) ranking the molecular features that exhibit a statistically significant difference in quantity between the samples contacted with the ligand and a sample that is not contacted with the ligand ("statistically significant molecular feature").

15 Claims, 23 Drawing Sheets

Specification includes a Sequence Listing.

(51) Int. Cl.
  *G01N 33/94*   (2006.01)
  *G01N 33/53*   (2006.01)
  *G16B 20/00*   (2019.01)
  *G01N 30/88*   (2006.01)

(52) U.S. Cl.
  CPC ..... *G16B 20/00* (2019.02); *G01N 2030/8831* (2013.01)

(56) References Cited

U.S. PATENT DOCUMENTS

2015/0133336 A1  5/2015  Nordlund et al.
2015/0140575 A1* 5/2015  Nordlund ............. G01N 33/948
                                                                435/7.1

OTHER PUBLICATIONS

Bagag et al., "Separation of peptides from detergents using ion mobility spectrometry," Rapid Communications in Mass Spectrometry, vol. 25, pp. 3436-3440, Sep. 6, 2011. (Year: 2011).*
Yates et al., "A Cloud Computing Implementation of Differential Mass Spectrometry: A Label Free Method for Proteomic Profiling," University of Pittsburgh: Research Poster, <http://www.bioms.pitt.edu/Poster/ASMS2014/dMS_Poster_06132014_02_40x23.pdf>, Jun. 13, 2014. (Year: 2014).*
Steketee, Pieter Christiaan, Investigating the mode of action of AN5568, a novel therapeutic against African trypanosomiasis, 265 pages (Mar. 2016).
Bagag, et al., "Separation of peptides from detergents using ion mobility spectrometry," *Rapid Commun. Mass spectrum.*, vol. 25, pp. 3436-3440 (2011).
Yates, et al., A Cloud Computing Implementation of Differential Mass Spectrometry: A Label Free Method for Proteomic Profiling, 1 page (Jun. 2014).
International Search Report and Written Opinion issued in International Patent Application No. PCT/US2017/053207, dated Apr. 9, 2018.
Almqvist, H. et al. CETSA screening identifies known and novel thymidylate synthase inhibitors and slow intracellular activation of 5-fluorouracil. *Nat Commun* 7, 11040 (2016), 11 pages.
Altschul et al., "Basic Local Alignment Search Tool," *J. Mol. Biol.*, vol. 215, pp. 403-410 (1990).
Altschul, et al., Nature Gent. vol. 6, pp. 119-129 (1994).
Broach, et al., "High-throughput screening fordrug discovery," *Nature* 384, 14-6 (1996).
Carnera, High throughput screening in drug discovery. *Clin Transl Oncol* 8, 482-90 (2006).
Corpet, "Multiple Sequence Alighment with Hierarchical Clustering," *Nucleic Acids Research*, vol. 16, No. 22, (1988).
Drews, J. Drug discovery: a historical perspective. *Science* 287, 1960-4 (2000).
Higgins, et al., "Clustal: A package for performing multiple sequence alignment on a microcomputer," *Genei*, vol. 73(1), pp. 237-244 (Dec. 1988).
Higgins, et al., "Fast and Sensitive Multiple Sequence Alignments on a Microcomputer," *Comput. Appl. Biosci.*, vol. 5(2), pp. 151-153 (Apr. 1989).
Jafari, R. et al. The cellular thermal shift assay for evaluating drug target interactions in cells. *Nat Protoc* 9, 2100-22 (2014).
Jensen, A.J., Martinez Molina, D. & Lundback, T. CETSA: a target engagement assay with potential to transform drug discovery. *Future Med Chem* 7, 975-8 (2015).
Kell, D.B., Dobson, P.D., Bilsland, E. & Oliver, S.G. The promiscuous binding of pharmaceutical drugs and their transporter-mediated uptake into cells: what we (need to) know and how we can do so. *Drug Discov Today* 18, 218-39 (2013).
Lavinder, J.J., Hari, S.B., Sullivan, B.J. & Magliery, T.J. High-throughput thermal scanning: a general, rapid dye-binding thermal shift screen for protein engineering. *J Am Chem Soc* 131, 3794-5 (2009).
Lee, J.A., Uhlik, M.T., Moxham, C.M., Tomandl, D. & Sall, D.J. Modern phenotypic drug discovery is a viable, neoclassic pharma strategy. *J Med Chem* 55, 4527-38 (2012).
Lomenick, B. et al. Target identification using drug affinity responsive target stability (DARTS). *Proc Natl Acad Sci U S A* 106, 21984-9 (2009).
Meng, F. et al. Quantitative analysis of complex peptide mixtures using FTMS and differential mass spectrometry. *J Am Soc Mass Spectrom* 18, 226-33 (2007).
Michalski, A., Cox, J. & Mann, M. More than 100,000 detectable peptide species elute in single shotgun proteomics runs but the majority is inaccessible to data-dependent LC-MS/MS. *J Proteome Res* 10, 1785-93 (2011).
Minde, D.P., Maurice, M.M. & Rudiger, S.G. Determining biophysical protein stability in lysates by a fast proteolysis assay, FASTpp. *PLoS One* 7, e46147 (2012).
Needleman et al., "A General Method Applicable to the Search for Similarities in the Amino Acid Sequence of Two Proteins," *J. Mol. Biol.*, vol. 48, pp. 443-453 (1970).
Pai, M.Y. et al. Drug affinity responsive target stability (DARTS) for small-molecule target identification. *Methods Mol Biol* 1263, 287-98 (2015).
Pantoliano, M.W. et al. High-density miniaturized thermal shift assays as a general strategy for drug discovery. *J Biomol Screen* 6, 429-40 (2001).
Pearson, et al., "Improved Tools for Biological Sequence Comparison," *Proc. Natl. Acad. Sci.*, vol. 85, pp. 2444-2448 (Apr. 1988).
Qian, W. et al. Novel combination of mitochondrial division inhibitor 1 (mdivi-1) and platinum agents produces synergistic pro-apoptotic effect in drug resistant tumor cells. *Oncotarget* 5, 4180-94 (2014).
Qian, W. et al. The combination of thioxodihydroquinazolinones and platinum drugs reverses platinum resistance in tumor cells by inducing mitochondrial apoptosis independent of Bax and Bak. *Bioorg Med Chem Lett* 25, 856-63 (2015).
Reinhard, F.B. et al. Thermal proteome profiling monitors ligand interactions with cellular membrane proteins. *Nat Methods* 12, 1129-31 (2015).
Savitski, M.M. et al. Tracking cancer drugs in living cells by thermal profiling of the proteome. *Science* 346, 12, pp. 55784 (2014), 12 pages.
Simaga, S. et al. Dipeptidyl III in malignant and non-malignant gynaecological tissue. *Eur J Cancer* 34, 399-405 (1998).
Simaga, S., Babic, D., Osmak, M., Sprem, M. & Abramic, M. Tumor cytosol dipeptidyl peptidase III activity is increased with histological aggressiveness of ovarian primary carcinomas. *Gynecol Oncol* 91, 194-200 (2003).
Stern, A.M., Schurdak, M.E., Bahar, I., Berg, J.M. & Taylor, D.L. A Perspective on Implementing a Quantitative Systems Pharmacology Platform for Drug Discovery and the Advancement of Personalized Medicine. *J Biomol Screen* 21, 521-34 (2016).
Wang, J. et al. A novel strategy for targeted killing of tumor cells: Induction of multipolar acentrosomal mitotic spindles with a quinazolinone derivative mdivi-1. *Mol Oncol* 9, 488-502 (2015).
Weber, P.C. & Salemme, F.R. Applications of calorimetric methods to drug discovery and the study of protein interactions. *Curr Opin Struct Biol* 13, 115-21 (2003).

(56) References Cited

OTHER PUBLICATIONS

Wiener, M.C., Sachs, J.R., Deyanova, E.G. & Yates, N.A. Differential mass spectrometry: a label-free LC-MS method for finding significant differences in complex peptide and protein mixtures. *Anal Chem* 76, 6085-96 (2004).

Zhao, X. et al. Differential mass spectrometry of rat plasma reveals proteins that are responsive to 17beta-estradiol and a selective estrogen receptor modulator PPT. *J Proteome Res* 7, 4373-83 (2008).

* cited by examiner

| Feature Mass | Monoisotopic Mass | RT | Charge | Peptide Sequence | Protein Description | Chorus AVERAGE | Chorus SD | Chorus CV | Manual AVERAGE | Manual SD | Manual CV |
|---|---|---|---|---|---|---|---|---|---|---|---|
| 713.37 | 713.37 | 150.8 | 2 | YISPDQLADLYK | Alpha-enolase | 1.3E+13 | 1.6E+12 | 13% | 8.4E+09 | 1.5E+09 | 17% |
| 706.40 | 706.40 | 115.8 | 2 | GALQNIIPASTGAAK | Glyceraldehyde-3-phosphate dehydrogenase | 8.9E+12 | 1.3E+12 | 14% | 6.0E+09 | 6.7E+08 | 11% |
| 766.40 | 765.90 | 123.0 | 2 | VPTANVSVVDLTCR | Glyceraldehyde-3-phosphate dehydrogenase | 6.6E+12 | 6.6E+11 | 10% | 4.5E+09 | 3.6E+08 | 8% |
| 981.97 | 980.97 | 138.7 | 2 | DATNVGDEGGFAPNILENK | Alpha-enolase | 4.1E+12 | 5.0E+11 | 12% | 2.9E+09 | 2.9E+08 | 10% |
| 758.89 | 758.39 | 123.6 | 2 | VCENIPIVLCGNK | GTP-binding nuclear protein Ran (Fragment) | 2.0E+12 | 1.6E+11 | 8% | 1.4E+09 | 7.5E+07 | 5% |
| 743.68 | 743.35 | 137.1 | 3 | YTPSGQAGAAASESLFVSNHAY | Isoform 2 of Fructose-bisphosphate aldolase A | 9.9E+11 | 1.5E+11 | 15% | 6.8E+08 | 8.1E+07 | 12% |
| 502.59 | 502.59 | 117.1 | 3 | VKEGMNIVEAMER | Peptidyl-prolyl cis-trans isomerase A | 8.0E+11 | 1.1E+11 | 14% | 5.8E+08 | 7.1E+07 | 12% |
| 764.88 | 764.38 | 123.1 | 2 | SLTNDWEDHLAVK | Isoform 2 of Heat shock protein HSP 90-alpha | 6.0E+11 | 8.6E+10 | 14% | 4.2E+08 | 5.0E+07 | 12% |
| 890.92 | 890.92 | 118.1 | 2 | VDATEESDLAQQYGVR | Protein disulfide-isomerase | 4.0E+11 | 4.2E+10 | 10% | 2.7E+08 | 4.4E+07 | 16% |
| 526.77 | 526.27 | 140.8 | 2 | MDELQLFR | Transitional endoplasmic reticulum ATPase | 2.0E+11 | 2.6E+10 | 13% | 1.4E+08 | 1.5E+07 | 11% |
| 681.36 | 680.69 | 169.7 | 3 | VVSQYSSLLSPMSVNAVMK | T-complex protein 1 subunit alpha | 1.0E+11 | 1.5E+10 | 15% | 1.3E+08 | 1.9E+07 | 15% |
| 450.93 | 450.93 | 112.2 | 3 | LIDLHSPSEIVK | 40S ribosomal protein S20 | 8.0E+10 | 8.6E+09 | 11% | 5.7E+07 | 5.0E+06 | 9% |
| 485.24 | 485.24 | 109.8 | 3 | KIENLCAMGFDR | Ubiquitin-conjugating enzyme E2 K | 6.0E+10 | 6.4E+09 | 11% | 3.9E+07 | 3.8E+06 | 10% |
| 748.07 | 748.06 | 131.5 | 3 | IIAEGANGPTTPEADKIFLER | Glutamate dehydrogenase 1, mitochondrial | 4.0E+10 | 4.5E+09 | 11% | 2.8E+07 | 3.0E+06 | 11% |
| 880.40 | 879.40 | 148.4 | 2 | EFAGEDTSDLFLEER | Exportin-1 | 2.0E+10 | 1.6E+09 | 8% | 1.5E+07 | 1.5E+06 | 10% |
| 399.74 | 398.73 | 73.4 | 2 | DPLNPIK | Inorganic pyrophosphatase | 1.0E+10 | 1.3E+09 | 13% | 6.7E+06 | 7.3E+05 | 11% |
| 650.70 | 650.36 | 146.5 | 2 | ELGENLDQILR | Importin-9 | 8.0E+09 | 1.1E+09 | 14% | 6.2E+06 | 8.1E+05 | 13% |
| 423.90 | 423.23 | 133.1 | 3 | ISMPDVDLHLK | Neuroblast differentiation-associated protein AHNAK | 6.0E+09 | 9.8E+08 | 16% | 3.5E+06 | 9.2E+05 | 26% |
| 875.41 | 873.73 | 141.9 | 3 | YMNGHSDVVMGLVSVNCESLHNR | Cystathionine gamma-lyase | 4.0E+09 | 4.4E+08 | 11% | n/d | n/d | n/d |
| 604.71 | 603.71 | 146.0 | 5 | NFTEVHPDYGSHIQALLDKYNAEKPK | Catalase | 2.0E+09 | 3.6E+08 | 18% | n/d | n/d | n/d |

FIG. 4

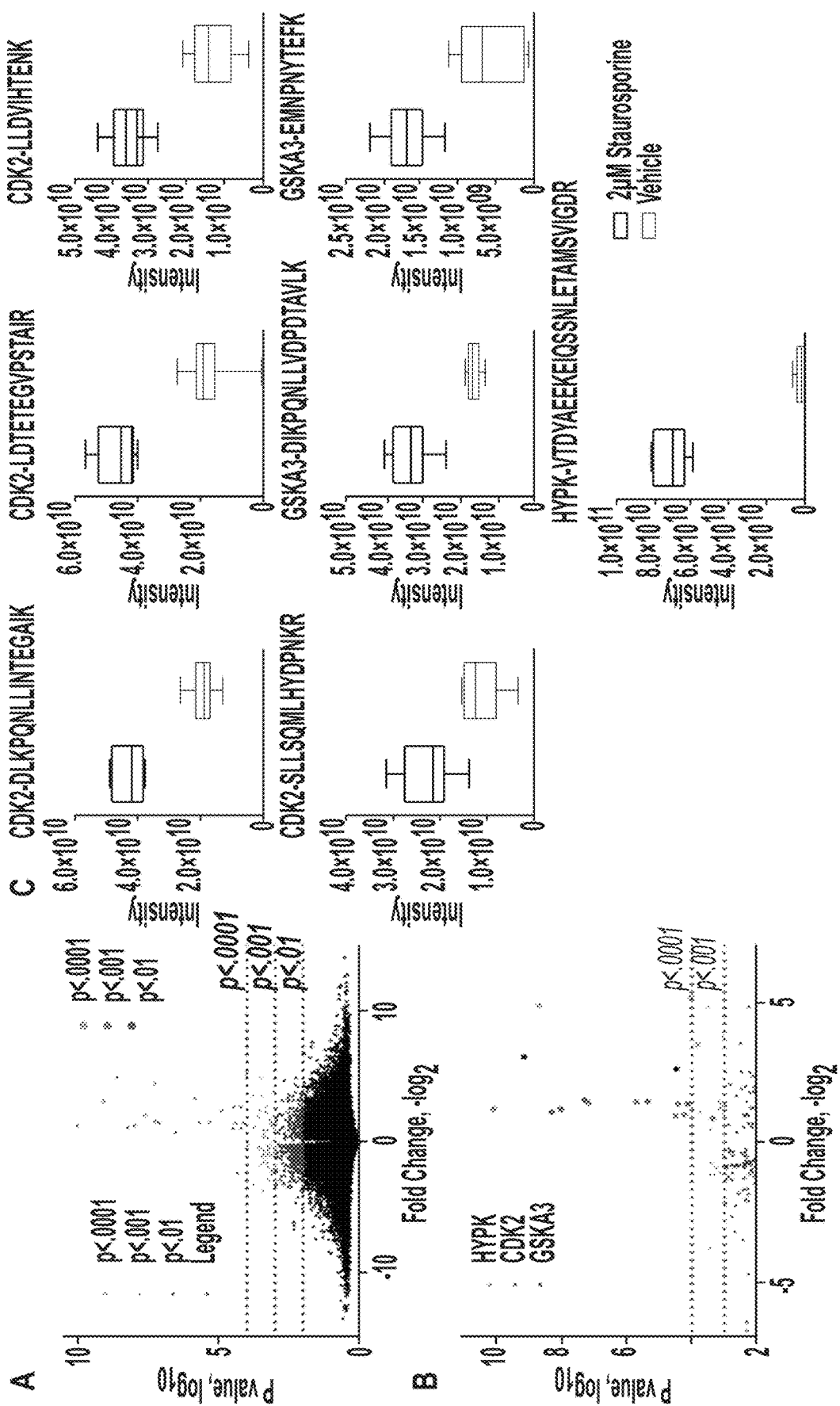
FIGS. 5A–C

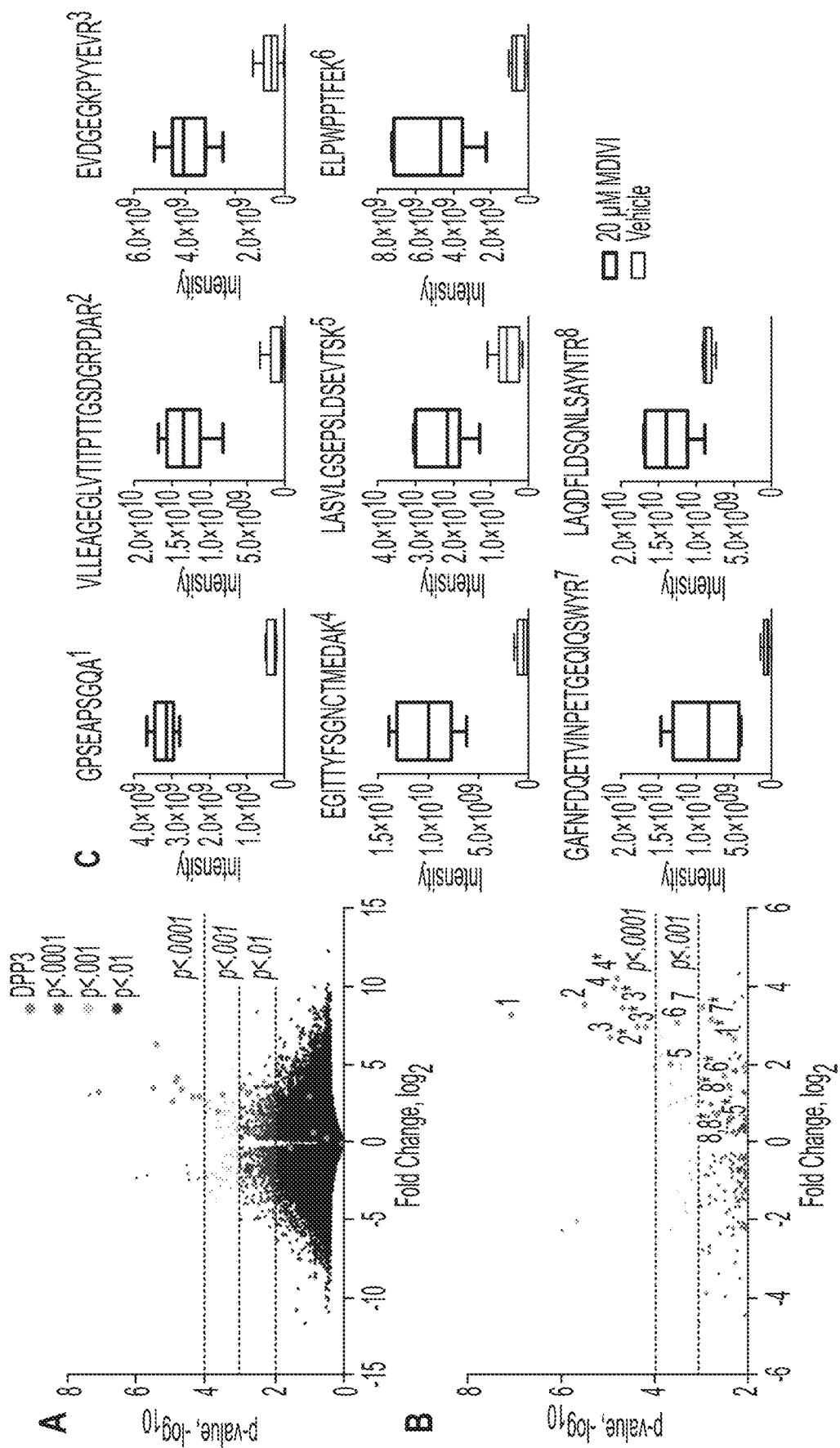
FIGS. 7A-C

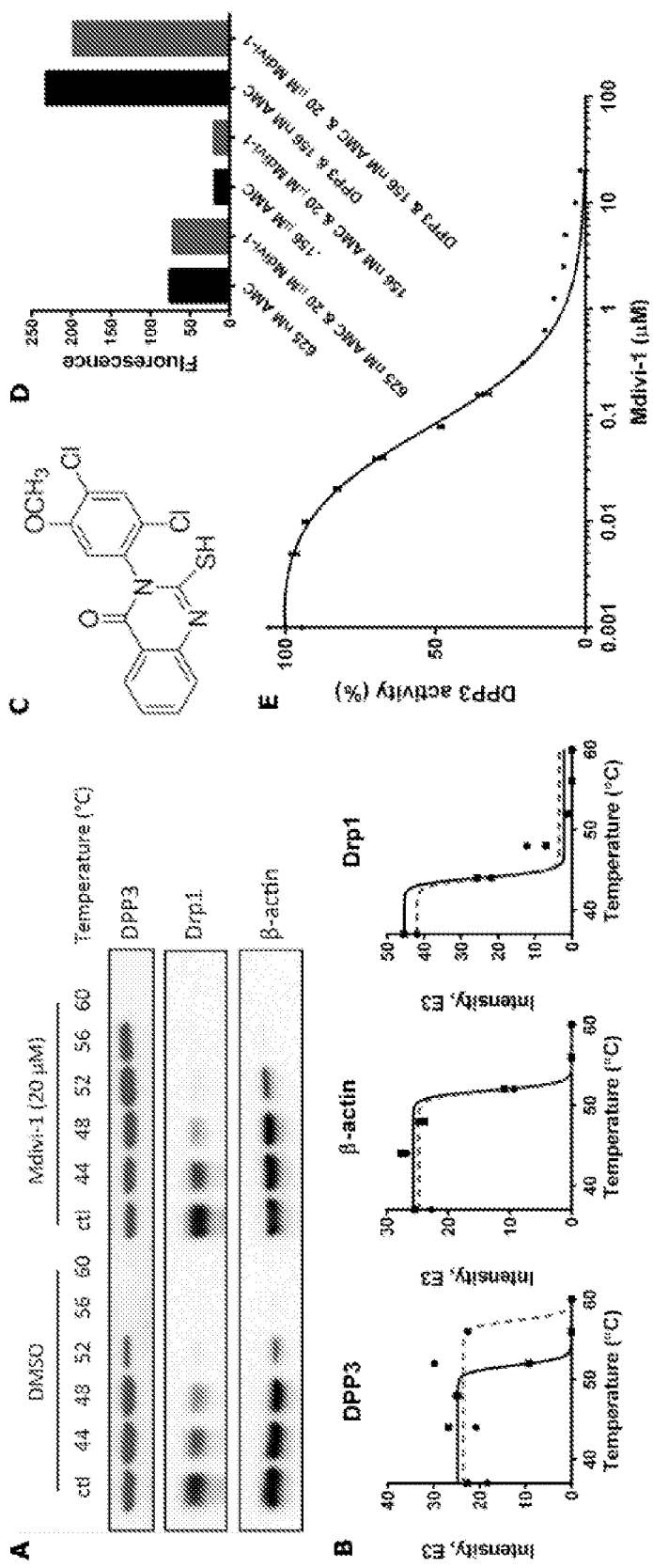
FIGS. 9A-E

SEQUENCE LISTING

```
<160> NUMBER OF SEQ ID NOS: 39

<210> SEQ ID NO 1
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1

Gly Pro Ser Glu Ala Pro Ser Gly Gln Ala
1               5                   10

<210> SEQ ID NO 2
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2

Val Leu Leu Glu Ala Gly Glu Gly Leu Val Thr Ile Thr Pro Thr Thr
1               5                   10                  15

Gly Ser Asp Gly Arg Pro Asp Ala Arg
            20                  25

<210> SEQ ID NO 3
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Glu Val Asp Gly Glu Gly Lys Pro Tyr Tyr Glu Val Glu Arg
1               5                   10

<210> SEQ ID NO 4
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Glu Gly Ile Thr Thr Tyr Phe Ser Gly Asn Cys Thr Met Glu Asp Ala
1               5                   10                  15

Lys

<210> SEQ ID NO 5
<211> LENGTH: 5
<212> TYPE: PRT
<213> ORGANISM: Artificial Sequence
```

```
<220> FEATURE:
<223> OTHER INFORMATION: Description of Artificial Sequence: Synthetic
      peptide

<400> SEQUENCE: 5

His His His His His
1               5

<210> SEQ ID NO 6
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

Glu Val Asp Gly Glu Gly Lys Pro Tyr Tyr Glu Val Arg
1               5                   10

<210> SEQ ID NO 7
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 7

Val Ile Leu Gly Ser Glu Ala Ala Gln Gln His Pro Glu Glu Val Arg
1               5                   10                  15

<210> SEQ ID NO 8
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 8

Tyr Ile Ser Pro Asp Gln Leu Ala Asp Leu Tyr Lys
1               5                   10

<210> SEQ ID NO 9
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 9

Gly Ala Leu Gln Asn Ile Ile Pro Ala Ser Thr Gly Ala Ala Lys
1               5                   10                  15

<210> SEQ ID NO 10
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 10

Val Pro Thr Ala Asn Val Ser Val Val Asp Leu Thr Cys Arg
1               5                   10
```

```
<210> SEQ ID NO 11
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 11

Asp Ala Thr Asn Val Gly Asp Glu Gly Gly Phe Ala Pro Asn Ile Leu
1               5                   10                  15

Glu Asn Lys

<210> SEQ ID NO 12
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 12

Val Cys Glu Asn Ile Pro Ile Val Leu Cys Gly Asn Lys
1               5                   10

<210> SEQ ID NO 13
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 13

Tyr Thr Pro Ser Gly Gln Ala Gly Ala Ala Ala Ser Glu Ser Leu Phe
1               5                   10                  15

Val Ser Asn His Ala Tyr
            20

<210> SEQ ID NO 14
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 14

Val Lys Glu Gly Met Asn Ile Val Glu Ala Met Glu Arg
1               5                   10

<210> SEQ ID NO 15
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 15

Ser Leu Thr Asn Asp Trp Glu Asp His Leu Ala Val Lys
1               5                   10

<210> SEQ ID NO 16
<211> LENGTH: 16
<212> TYPE: PRT
```

<213> ORGANISM: Artificial Sequence
<220> FEATURE:
<223> OTHER INFORMATION: Description of Artificial Sequence: Synthetic
      peptide

<400> SEQUENCE: 16

Val Asp Ala Thr Glu Glu Ser Asp Leu Ala Gln Gln Tyr Gly Val Arg
1               5                   10                  15

<210> SEQ ID NO 17
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 17

Met Asp Glu Leu Gln Leu Phe Arg
1               5

<210> SEQ ID NO 18
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 18

Val Val Ser Gln Tyr Ser Ser Leu Leu Ser Pro Met Ser Val Asn Ala
1               5                   10                  15

Val Met Lys

<210> SEQ ID NO 19
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 19

Leu Ile Asp Leu His Ser Pro Ser Glu Ile Val Lys
1               5                   10

<210> SEQ ID NO 20
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 20

Lys Ile Glu Asn Leu Cys Ala Met Gly Phe Asp Arg
1               5                   10

<210> SEQ ID NO 21
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 21

Ile Ile Ala Glu Gly Ala Asn Gly Pro Thr Thr Pro Glu Ala Asp Lys
1               5                   10                  15

Ile Phe Leu Glu Arg
            20

<210> SEQ ID NO 22
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 22

Glu Phe Ala Gly Glu Asp Thr Ser Asp Leu Phe Leu Glu Glu Arg
1               5                   10                  15

<210> SEQ ID NO 23
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 23

Asp Pro Leu Asn Pro Ile Lys
1               5

<210> SEQ ID NO 24
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 24

Glu Leu Gly Glu Asn Leu Asp Gln Ile Leu Arg
1               5                   10

<210> SEQ ID NO 25
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 25

Ile Ser Met Pro Asp Val Asp Leu His Leu Lys
1               5                   10

<210> SEQ ID NO 26
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 26

Tyr Met Asn Gly His Ser Asp Val Val Met Gly Leu Val Ser Val Asn
1               5                   10                  15

Cys Glu Ser Leu His Asn Arg
            20

<210> SEQ ID NO 27
<211> LENGTH: 26
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 27

Asn Phe Thr Glu Val His Pro Asp Tyr Gly Ser His Ile Gln Ala Leu
1               5                   10                  15

Leu Asp Lys Tyr Asn Ala Glu Lys Pro Lys
            20                  25

<210> SEQ ID NO 28
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 28

Asp Leu Lys Pro Gln Asn Leu Leu Ile Asn Thr Glu Gly Ala Ile Lys
1               5                   10                  15

<210> SEQ ID NO 29
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 29

Leu Asp Thr Glu Thr Glu Gly Val Pro Ser Thr Ala Ile Arg
1               5                   10

<210> SEQ ID NO 30
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 30

Leu Leu Asp Val Ile His Thr Glu Asn Lys
1               5                   10

<210> SEQ ID NO 31
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 31

Ser Leu Leu Ser Gln Met Leu His Tyr Asp Pro Asn Lys Arg
1               5                   10

<210> SEQ ID NO 32
<211> LENGTH: 17

<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 32

Asp Ile Lys Pro Gln Asn Leu Leu Val Asp Pro Asp Thr Ala Val Leu
1               5                   10                  15
Lys

<210> SEQ ID NO 33
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 33

Glu Met Asn Pro Asn Tyr Thr Glu Phe Lys
1               5                   10

<210> SEQ ID NO 34
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 34

Val Thr Asp Tyr Ala Glu Glu Lys Glu Ile Gln Ser Ser Asn Leu Glu
1               5                   10                  15
Thr Ala Met Ser Val Ile Gly Asp Arg
            20                  25

<210> SEQ ID NO 35
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 35

Leu Ala Ser Val Leu Gly Ser Glu Pro Ser Leu Asp Ser Glu Val Thr
1               5                   10                  15
Ser Lys

<210> SEQ ID NO 36
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 36

Glu Leu Pro Trp Pro Pro Thr Phe Glu Lys
1               5                   10

<210> SEQ ID NO 37
<211> LENGTH: 24
<212> TYPE: PRT
<213> ORGANISM: Artificial Sequence

```
<220> FEATURE:
<223> OTHER INFORMATION: Description of Artificial Sequence: Synthetic
      peptide

<400> SEQUENCE: 37

Gly Ala Phe Asn Phe Asp Gln Glu Thr Val Ile Asn Pro Glu Thr Gly
1               5                  10                  15

Glu Gln Ile Gln Ser Trp Tyr Arg
            20

<210> SEQ ID NO 38
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 38

Leu Ala Gln Asp Phe Leu Asp Ser Gln Asn Leu Ser Ala Tyr Asn Thr
1               5                  10                  15

Arg

<210> SEQ ID NO 39
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 39

Gly Pro Ser Phe Asp Val Gln Val Gly Leu His Glu Leu Leu Gly His
1               5                  10                  15

Gly Ser Gly Lys
            20
```

METHODS FOR IDENTIFYING PROTEINS THAT BIND LIGANDS

CROSS-REFERENCE TO RELATED APPLICATIONS

This application is the U.S. National Stage of International Patent Application No. PCT/US2017/053207, filed Sep. 25, 2017, which claims priority from U.S. Provisional Patent Application No. 62/399,777, filed on Sep. 26, 2016, the contents of these applications are incorporated herein by reference in their entirety.

GOVERNMENT LICENSE RIGHTS

This invention was made with government support under CA047904 and AG043376 awarded by the National Institutes of Health. The government has certain rights in the invention.

SEQUENCE LISTING

The instant application contains a Sequence Listing which has been submitted electronically in ASCII format and is hereby incorporated by reference in its entirety. Said ASCII copy, created on Mar. 18, 2020, is named 076333-0924 SL.txt and is 11,303 bytes in size.

FIELD

This disclosure relates to methods for identifying proteins capable of binding a ligand.

BACKGROUND

Pharmaceutical drugs and chemical probes work by binding to one or more proteins present in cells and biological systems to induce a conformational or other change that regulates chemical reactions and the physiology of living organisms. Previously, drug-protein binding has been inferred from shotgun proteomic studies that identify large numbers of possible candidates in affinity capture, enzymatic digestion, and/or thermal stability experiments.

The identification of therapeutically relevant proteins that bind small molecule drugs provides the foundation for the pharmaceutical industry and has been the subject of a wide range of investigations that make use of practically all molecular techniques for biological research.[1] One small portion of research into important drug targets exploits the differential stability of proteins that bind small molecules and the utility of mass spectrometry to measure these changes in complex mixtures. This recently led to a major advance that has the potential to open new technological opportunities for the unbiased identification of novel drug-targets by proteomics.[2-4] With the ability to analyze entire proteomes under physiological conditions, it may be possible to define the complete binding profile of small organic molecules that exhibit novel therapeutic activity. This is important since it is well known that on average every approved drug interacts with at least six distinct proteins.[5] Therefore, any efficacious response could be due to one or more molecular targets, while some interactions could cause on or off-target effects that are toxic.[6] Robust and efficient target identification strategies are also of importance to phenotypic drug discovery; especially when applied as part of a quantitative systems pharmacology (QSP) approach that hinge on the ability to identify protein targets once phenotypically active compounds have been identified.[6,7]

Established methods for characterizing protein-ligand interactions often involve high-throughput screening compound libraries against single purified proteins.[8-12] Contemporary proteomic methods such as fast parallel proteolysis (FASTPP), drug affinity responsive target stability (DARTS), and cellular thermal shift assay (CETSA) reverse this paradigm by screening entire proteomes in a single experiment. FASTPP and DARTS exploit a reduction in protease susceptibility of the target protein upon drug binding.[3,4,13] CETSA reveals drug-protein binding in cells and complex protein extracts by measuring the relative abundance of proteins that remain in solution following a heating and precipitation process.[2,14-16] Proteins that bind small molecule drugs remain in solution at higher temperatures, generating a "shift" in the protein stability curves. Each of these methods have been shown to be widely applicable because they require no chemical modification of the drug and are independent of the mechanism of action.

The investigation of complex proteomic mixtures, as opposed to purified proteins, underscores the importance of experimental design and analytical approach. The methods used must not only identify putative drug targets, but also be able to prioritize a limited number of results for evaluation in follow up studies. Savitski et al. coupled CETSA with TMT labeling technology to identify large numbers of proteins and prioritize based on a change in the thermal stability curve. The experimental design utilized multiple samples across a temperature range, but only one sample per temperature; and only analyzed the subset of data that was initially identified by tandem mass spectrometry (MS/MS).[16,17] As shown by Michalski et al., the vast majority of peptidic signals (84%) are not selected for MS/MS; only 10% of all peptides are identified.[18]

Accordingly, there is a need for an analysis of multiple samples of a large number of proteins in which all peptidic signals are quantified and evaluated prior to identification of the peptides. Additionally, there is a need for an unbiased analysis of large numbers of proteins to determine which may bind to a small molecule drug.

SUMMARY

In one aspect, provided herein are methods of identifying a protein capable of binding a ligand, the method comprising: (a) contacting the ligand with two or more samples comprising a plurality of proteins in a solution; (b) differentiating the proteins bound to the ligand ("bound proteins") from the proteins that are not bound to the ligand ("unbound proteins") in each sample; (c) denaturing and digesting the bound proteins to form a plurality of peptides in each sample; (d) quantifying a plurality of molecular features contained in the plurality of peptides in each sample, wherein the molecular features are defined as having a mass to charge ratio, retention time, and peak intensity as measured by mass spectrometry; (e) ranking the molecular features that exhibit a statistically significant difference in quantity between the samples contacted with the ligand and a sample that is not contacted with the ligand ("statistically significant molecular feature"); (f) identifying one or more amino acid sequences of the statistically significant molecular features that are highly ranked; and (g) identifying a protein that comprises the amino acid sequences of step (f).

In some embodiments, step (a) comprises solubilizing the proteins using a surfactant, a detergent, or any combination thereof. In some embodiments, the detergent comprises octylglucyl pyranoside or dodecyl maltoside.

In some embodiments, step (b) comprises heating each sample to a temperature such that the solubility of the bound protein is different in the sample contacted with the ligand than the solubility of that same protein in a sample not contacted with the ligand. In some embodiments, each sample is heated to a temperature of from about 40° C. to about 65° C. In some embodiments, each sample is heated from about 48° C. to about 56° C. In some embodiments, each sample is heated to a temperature of about 56° C.

In some embodiments, step (b) comprises titrating each sample with a solution to lower the dielectric constant such that the solubility of the bound protein is different in the sample contacted with the ligand than the solubility of that same protein in a sample not contacted with the ligand. In some embodiments, each sample is titrated with acetone or methanol.

In some embodiments, the plurality of peptides of step (c) are analyzed using nano-scale liquid chromatographic tandem mass spectrometry prior to step (d).

In some embodiments, step (e) comprises using differential mass spectrometry.

In some embodiments, the methods further comprise assigning the molecular features to an isotope group characterized by a chemical formula and an isotope distribution.

In some embodiments, ranking the statistically significant molecular features comprises statistical and practical filtering.

In some embodiments, the statistically significant molecular features that are determined to still be significant based upon the statistical and practical filtering are highly ranked.

In some embodiments, the statistical filtering comprises t-tests.

In some embodiments, the practical filtering comprises excluding any statistically significant molecular features that are not present in at least two-thirds of the samples contacted with the ligand.

In some embodiments, the practical filtering comprises excluding any statistically significant molecular features that were the only significant features in a single isotope group with a p value of less than about 0.01 based on the statistical filtering.

In some embodiments, step (e) comprises CHORUS web application for storing, sharing, visualizing, and analyzing spectrometry files.

In some embodiments, step (g) comprises comparing the amino acid sequences of the statistically significant molecular features with a protein database and identifying which proteins of the protein database contain the statistically significant molecular features.

The inventions described and claimed herein have many attributes and embodiments including, but not limited to, those set forth or described or referenced in this Summary. It is not intended to be all-inclusive and the inventions described and claimed herein are not limited to or by the features or embodiments identified in this Summary, which is included for purposes of illustration only and not restriction. Additional embodiments may be disclosed in the Brief Description of the Drawings and Detailed Description below.

BRIEF DESCRIPTION OF THE DRAWINGS

FIG. 3 shows illustrations horizontally from right to left of the data types (top) that are transformed by computational services (middle) that are executed on distributed CPU's, and resulting information (bottom) that are stored by the system. A publically accessible instance of the dMS platform is available at www.chorusproject.org along with the data and results reported in this manuscript.

FIG. 4 is a table comparing the CHORUS quantification precision and manual quantification methods. 20 features across a wide intensity range were blindly selected in decreasing steps of feature intensity across 14 pooled samples run non-consecutively. Quantification was performed in CHORUS as well as using the manual tools in the Thermo XCalibur mass spectrometer software suite. Coefficient of variance ranged from 8-18% with an average coefficient of variance of 12.6% for the CHORUS quantification. Coefficient of variance ranged from 5-26% for the manual tools, with an average coefficient of variance of 12%. Manual tools were not able to select the two lowest intensity features for analysis. Figure discloses SEQ ID NOS 8-27, respectively, in order of appearance.

FIGS. 5A-C are graphical illustrations of the DISRUPT analysis of staurosporine treated K562 cells compared to the control. FIG. 5A is a volcano plot of $\log_2$ transform fold change vs. p value showing features, n=200,256, quantified in 20 samples by nano-LC/MS. Displayed features were detected in six of ten samples per condition. Dashed horizontal lines show $p<.01$, $p<0.001$, and $p<.0001$ thresholds for an unpaired Student's two-tailed equal variance t-test. FIG. 5B is a volcano plot showing 140 features that meet the following selection criteria: $n \geq 2$ significant features per isotope group where p≤0.01. The fifteen features with p<0.0001 were identified as peptides with sequences that uniquely belong to proteins CDK2, GSKA3, and HYPK; two of these proteins are canonical targets of staurosporine. FIG. 5C depicts box and whiskers plots showing the minimum and maximum intensity as well as the $25^{th}$ and $75^{th}$ percentile of intensities across all replicates of features of greatest significance and the corresponding peptide amino acid sequence that was identified by tandem mass spectrometry. FIG. 5C shows data for hundreds of thousands of high-resolution MS features and the precise selection and ranking of a small number of highly significant features that correspond to proteins that are known to bind staurosporine. FIG. 5C discloses SEQ ID NOS 28-34, respectively, in order of appearance.

FIG. 6A discloses SEQ ID NO: 30. FIG. 6B discloses SEQ ID NO: 33. FIG. 6C discloses SEQ ID NO: 34. FIG. 6D discloses SEQ ID NO: 32. FIG. 6E discloses SEQ ID NO: 28. FIG. 6F discloses SEQ ID NO: 29. FIG. 6G discloses SEQ ID NO: 31.

FIGS. 7A-C are graphical illustrations of a DISRUPT analysis of mdivi-1 treated a2780cis immortalized cancer cells. FIG. 7A is a volcano plot showing 182,171 features quantified in 12 samples using identical selection criteria as in FIG. 3. FIG. 7B shows the data reduction as described in FIG. 3 that excludes all but 218 features with p<0.01. Eight of nine features found to have a significance of p<0.0001 and a positive fold change were identified as peptides with amino acid sequences GPSEAPSGQA (SEQ ID NO:1), VLLEAGEGLVTITPTTGSDGRPDAR (SEQ ID NO: 2), EVDGEGKPYYEVER (SEQ ID NO: 3), and EGIT-TYFSGNCTMEDAK (SEQ ID NO: 4) belonging to DPP3. FIG. 7C shows box plots of numbered features that were identified as DPP3 peptides with p<0.01, showing significantly increased protein intensity in samples treated with mdivi-1. Data points marked with an asterisk were additional isotope group members for the identified peptides. FIG. 7C discloses SEQ ID NOS 1-2, 6, 4 and 35-38, respectively, in order of appearance.

FIG. 8A discloses SEQ ID NO: 2. FIG. 8B discloses SEQ ID NO: 37. FIG. 8C discloses SEQ ID NO: 38. FIG. 8D discloses SEQ ID NO: 35. FIG. 8E discloses SEQ ID NO: 6. FIG. 8F discloses SEQ ID NO: 4. FIG. 8G discloses SEQ ID NO: 39.

FIGS. 9A-E represent the biochemical validation that mdivi-1 binds to, and inhibits, the function of DPP3. FIG. 9A is a western blotting analysis of DPP3 with and without mdivi-1 as a function of temperature showing a significant increase in signal with temperature when treated with mdivi-1 as compared to vehicle. β-actin was probed as a control on the same blot; it shows no change due to drug treatment-related protein intensity decline, nor does DRP1, a prospective binding target of mdivi-1. FIG. 9B represents thermal shift curves over a wide temperature range from Western blotting analysis for DPP3, β-actin, and DRP1; a strong shift was seen for DPP3, no shifts were observed for β-actin or DRP1. FIG. 9C shows the structure of mdivi-1, a thioxodihydroquinazolinone compound that is a prospective treatment for cisplatin resistant cancers. FIG. 9D shows the control data for fluorescent activity assay showing alteration of DPP3 function with mdivi-1 treatment, thus establishing that mdivi-1 absent DPP3 caused no significant change in fluorescence level of peptide substrate. As illustrated in the final bar, the addition of mdivi-1 10 minutes post reaction showed no significant difference from DPP3 with substrate but without mdivi-1.

FIG. 9E shows DPP3 activity was measured using a fluorescent polypeptide; the n-terminal fluorophore is cleaved by DPP3 reducing the fluorescence in the sample. The assay demonstrates that mdivi-1 has an $IC_{50}$ of 70 nM upon DPP3 activity.

FIG. 10 discloses SEQ ID NOS 1-2, 6, 4, 4, 6, 2 and 6, respectively, in order of appearance.

DETAILED DESCRIPTION

Figure 1:
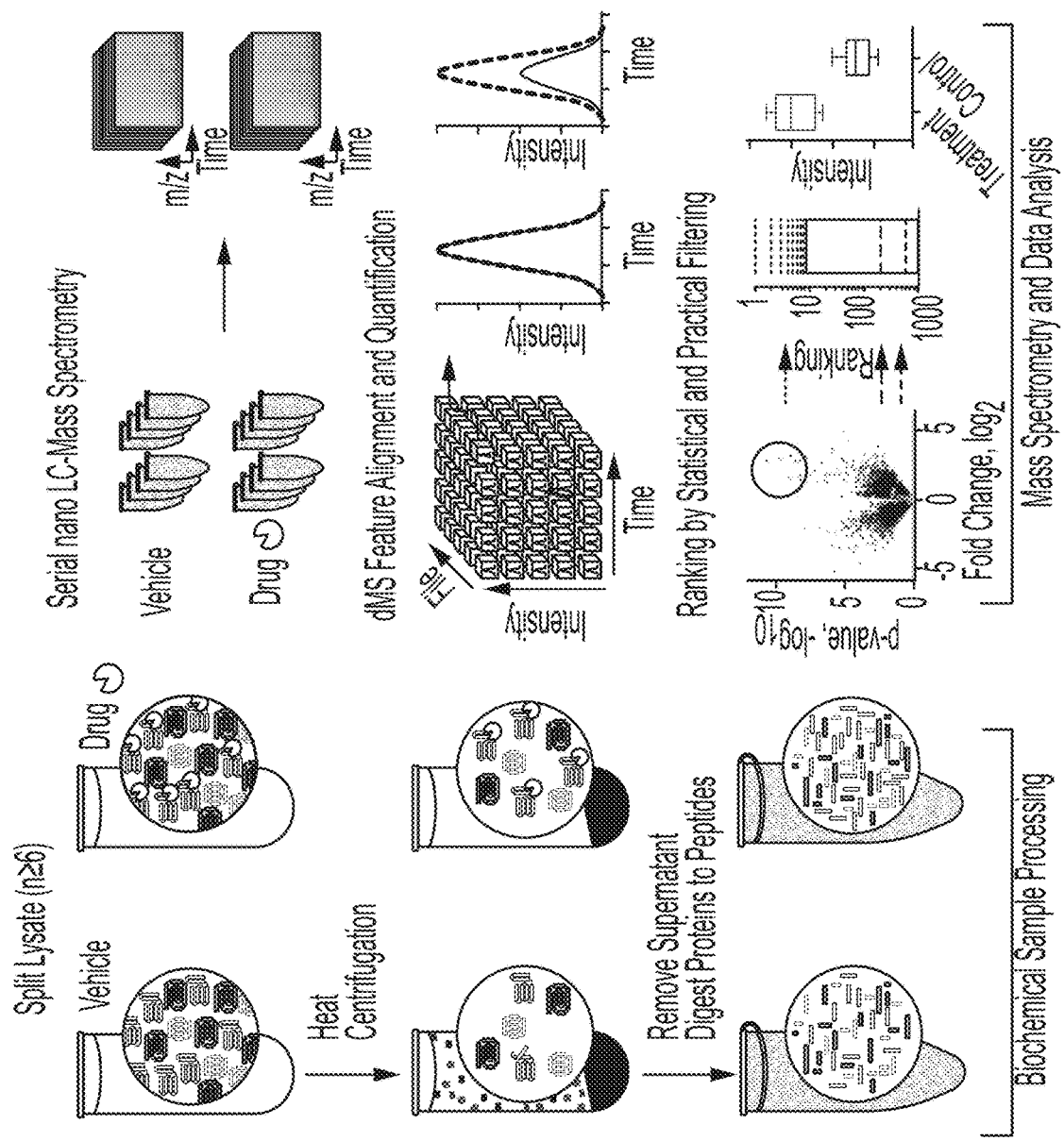
FIG. 1 is a schematic illustration of the differential intensity screening and ranking of unknown protein targets (DISRUPT) workflow. Samples of equal protein amount and concentration, in groups of $n \geq 6$, are treated with drug and vehicle. Drug binding stabilizes proteins in solution. Following an incubation period, samples are heated. Drug stabilized proteins are less likely to denature and agglutinate due to heating than vehicle treated proteins, a difference that can be observed following centrifugation. The remaining soluble proteins are digested to peptides, leaving a greater number of peptides from heat stabilized proteins in solution. Samples are run in serial on a nano liquid chromatography high-resolution mass spectrometer resulting in chromatograms of individual isotopic peptides or "features." Differential mass spectrometry tools quantify these features and align them across all mass spectrometer runs, allowing for quantification of drug binding effect across files. Applying statistical and practical filters, hundreds of thousands of features can be sorted and ranked, resulting in a highly confident list of prospective drug-binding proteins.

Provided herein is a method termed differential intensity screening and ranking of unknown protein targets (DISRUPT) that employs label-free differential mass spectrometry to measure differences in protein stability at a single temperature, introduced in FIG. 1. DISRUPT ranks hundreds of thousands of high-resolution mass spectrometry features by statistical significance. This methodology was validated by profiling the binding of staurosporine, a non-specific protein kinase inhibitor, to cytosolic proteins and prioritizing a ranked list of statistically significant signals that were subsequently identified as canonical interactions. Afterwards, mdivi-1, a putative ovarian cancer treatment in tumors that have shown resistance to cisplatin, with no known molecular target or mode of action was then studied.[22-24] DISRUPT ranked dipeptidyl peptidase 3 (DPP3) as the top putative target of mdivi-1 and this finding was subsequently validated by orthogonal quantitative and functional assays.

Differential mass spectrometry, as described by Yates et al., overcomes the obstacles faced by established methods by quantifying 100% of the signals accessible by mass spectrometry (MS) prior to identification.[19-21] This label-free approach supports large multi-factorial experimental designs and prioritizes signals that exhibit a statistically significant difference in abundance across groups of samples. An added benefit is that experiments are truly unbiased and can be performed blinded. No a priori selection criteria or expectation of a specific curve is required for the methodology to function. Additionally, the DISRUPT methodology provides for the identification of a small number of highly likely protein targets of a small molecule drug out of samples containing potentially thousands of proteins, thereby minimizing the time and costs associated with assessing whether the highly likely protein targets are indeed true protein targets.

I. Methods

In one aspect, provided herein are methods of identifying a protein capable of binding a ligand, the method comprising: (a) contacting the ligand with two or more samples comprising a plurality of proteins in a solution; (b) differentiating the proteins bound to the ligand ("bound proteins") from the proteins that are not bound to the ligand ("unbound proteins") in each sample; (c) denaturing and digesting the bound proteins to form a plurality of peptides in each sample; (d) quantifying a plurality of molecular features contained in the plurality of peptides in each sample, wherein the molecular features are defined as having a mass to charge ratio, retention time, and intensity as measured by mass spectrometry; (e) ranking the molecular features that exhibit a statistically significant difference in quantity between the samples contacted with the ligand and a sample that is not contacted with the ligand ("statistically significant molecular feature"); (f) identifying one or more amino acid sequences of the statistically significant molecular features that are highly ranked; and (g) identifying a protein that comprises the amino acid sequences of step (f).

It is well-understood in the art that when proteins bind to a ligand, such as a small molecule drug, such binding changes the physical conformation of the protein/ligand complex. Due to the change in the physical conformation of the protein/ligand complex, the solubility of the protein/ligand complex changes. Accordingly, the methods provided herein rely on this solubility change in the protein/ligand complex by detecting which proteins exhibit a difference in solubility in a sample contacted with the ligand as compared to the solubility of the same protein in a sample not contacted with the ligand.

The methods provided herein can take advantage of ligand/protein stabilization by disordering the system through heat or chemical denaturation. A ligand bound protein is a stable protein, so it can withstand more heat or chemical denaturation prior to agglutination/precipitation. Methods of using heat or chemical denaturation to alter the stability of proteins are well-known in the art. For example, as disclosed in U.S. Patent Application No. 2015/0133336, which is hereby incorporated by reference in its entirety, a critical feature of CETSA methodology is the use of heat to alter the stability of the protein. As noted above, chemical denaturation can also be used to change the stability of the protein.

It is well-known in the art that detergents may be used to study insoluble membrane proteins, because they can withstand or actually improve their abilities in heat/denaturants and do not interfere with complex function. Accordingly, the methods provided herein can rely on the known changes to conformational stability that occur in ligand binding for membrane proteins when attempting to detergent solubilize. A different proportion of protein will solubilize in the same amount of detergent if it is or is not bound to a ligand. This difference can be utilized to identify which proteins bind the ligand. Thus, in some embodiments, the methods provided herein allow for an analysis of normally insoluble proteins to determine whether the insoluble proteins are targets of a ligand by solubilizing the normally insoluble proteins with the use of a surfactant, detergent, or any combination thereof.

Suitable, non-limiting examples of surfactants that can be used in the methods provided herein include those that are well-known in the art. In some embodiments, suitable surfactants are those that maintain native states, that do not interfere with protein ligand binding, that are mass spectrometry compatible, and that do not interfere with protein/protein binding in existing complexes.

Suitable detergents that can be used in the methods provided herein include detergents that maintain native states, that do not interfere with protein ligand binding, that are mass spectrometry compatible, and that do not interfere with protein/protein binding in existing complexes. Non-limiting examples of suitable detergents that can be used include octylglucyl pyranoside, dodecyl maltoside, and the like. In some embodiments, the detergent comprises octylglucyl pyranoside. In some embodiments, the detergent comprises dodecyl maltoside. In some embodiments, the detergent comprises a combination of octylglucyl pyranoside and dodecyl maltoside.

In some embodiments, differentiating the bound proteins from the unbound proteins comprises heating each sample to a temperature such that the solubility of the bound protein is different in the sample contacted with the ligand than the solubility of that same protein in a sample not contacted with the ligand. In some embodiments, each sample is heated to a temperature of from about 40° C. to about 65° C., or any amount in-between these two values, such as but not limited to about 41° C., about 42° C., about 43° C., about 44° C., about 45° C., about 46° C., about 47° C., about 48° C., about 49° C., about 50° C., about 51° C., about 52° C., about 53° C., about 54° C., about 55° C., about 56° C., about 57° C., about 58° C., about 59° C., about 60° C., about 61° C., about 62° C., about 63° C., about 64° C., or about 65° C. In some embodiments, each sample is heated from about 48° C. to about 56° C. In some embodiments, each sample is heated to a temperature of about 56° C.

In some embodiments, when a surfactant, detergent, or any combination thereof is used to solubilize the proteins in the samples, the samples are not heated. In some embodiments, when a surfactant, detergent, organic acid, or any combination thereof is used to solubilize the proteins in the samples, the samples are heated.

In some embodiments, differentiating the bound proteins from the unbound proteins comprises titrating each sample with a solution to lower the dielectric constant such that the solubility of the bound protein is different in the sample contacted with the ligand than the solubility of that same protein in a sample not contacted with the ligand. In some embodiments, the sample is titrated with acetone. In some embodiments, the sample is titrated with methanol. In some embodiments, the sample is titrated with a combination of acetone and methanol. Other non-limiting examples of titrating solutions to lower the dielectric constant of the unbound proteins are well known in the art.

Other methods of differentiating bound proteins and unbound proteins are also well-known in the art. Non-limiting examples of such methods include thermofluor binding to hydrophobic regions exposed during the melting of a protein, which are exposed at differential rates in ligand bound and non-ligand bound proteins; thiol specific dyes binding to cysteine exposed during the melting of a protein; and employing ligands tagged for enrichment or visualization, such as 5-his (SEQ ID NO: 5), glutathione-s-transferase, or fluorescent tag and bead immobilized ligands.

In some embodiments, the bound proteins and unbound proteins in each sample are differentiated by solubilizing or maintaining the solubility of the bound proteins while the unbound proteins remain non-solubilized or precipitate out of solution. Once the bound proteins and unbound proteins are differentiated, in some embodiments, the non-solubilized, unbound proteins are removed from each sample by methods well-known in the art. In some embodiments, the non-solubilized unbound proteins are removed from the sample using centrifugation. Centrifugation is a well-known technique in the art to remove any precipitates from a solution. In some embodiments, the non-solubilized unbound proteins are removed from the sample using filtration. Filtration involves filtering away the non-solubilized unbound proteins from the solubilized bound proteins. In some embodiments, the non-solubilized unbound proteins are removed from the sample using both centrifugation and filtration, including centrifugation followed by filtration or filtration followed by centrifugation.

In some embodiments, after the differentiation of the bound and unbound proteins, the bound proteins are denatured and digested to form a plurality of peptides, which may be quantified through well-known methods of proteomic analysis. In some embodiments, the peptides of the plurality may be analyzed using mass spectrometry techniques. Mass spectrometry techniques for identifying peptides and/or proteins are well known in the art. For example, U.S. Pat. No. 6,906,320 "Mass Spectrometry Data Analysis Techniques," incorporated herein by reference in its entirety, discloses methods for identification of peptides and/or proteins using mass spectrometry. In some embodiments, the mass spectrometry techniques may be used to identify molecular features contained in the plurality of peptides. In some embodiments, these molecular features may be defined by a mass-to-charge ratio, retention time, and peak intensity.

In some embodiments, the mass spectrometry techniques comprise nano-scale liquid chromatographic tandem mass spectrometry. In some embodiments, the peptides are separated by reversed phase liquid chromatography, ionized by electrospray ionization, and analyzed with a hybrid ion trap/high-resolution Fourier transform mass spectrometer or a high resolution quantitative time of flight instrument (QTOF). In some embodiments, high resolution mass spectra of a peptide may be measured at a frequency of approximately 1 Hz. The mass spectra of each peptide may be used to categorize the plurality of peptides into distinct molecular features defined by a mass-to-charge ratio, retention time, and peak intensity. The techniques involved in identifying peptides and/or proteins using nano-scale liquid chromatographic tandem mass spectrometry are readily understood in the art.

In some embodiments, after quantification of each distinct molecular feature contained in the plurality of peptides, molecular features that exhibit a statistically significant difference in quantity between the samples contacted with the ligand and a sample that is not contacted with the ligand are ranked. Without being bound by theory, it is expected that after binding to the ligand, the bound proteins undergo a solubility change such that there is a difference in the concentration of the proteins that bind to the ligand in the samples contacted with the ligand as compared to the concentration of the same proteins in the samples not contacted with the ligand. Accordingly, it is expected that the proteins that exhibit a difference in concentration between the samples contacted with the ligand and the samples not contacted with the ligand are the proteins that bind to the ligand. In some embodiments, the concentration of the proteins that bind to the ligand is higher in the samples contacted with the ligand than in the samples not contacted with the ligand. In some embodiments, the concentration of the proteins that bind to the ligand is lower in the samples contacted with the ligand than in the samples not contacted with the ligand.

In some embodiments, the ranking comprises the use of differential mass spectrometry.

In some implementations, the spectrometry RAW files from the mass spectrometer is supplied to an analysis unit. The analysis unit can be a component of the mass spectrometer or can be a stand-alone device that electronically receives the RAW files. In some implementations, the analysis unit is a cloud based system that can interface with other local or cloud based systems. For example, in some embodiments, the ranking comprises the CHORUS web application for storing, sharing, visualizing, and analyzing spectrometry files. CHORUS is available online at www.chorusproject.org. The analysis unit can include a filtering unit. The filtering unit can remove noise and background signals from the RAW files. The analysis unit can also include an image processing unit. The image processing unit can identify the peaks within the filtered spectrometry files. In some embodiments, the ranking by the analysis unit can also include assigning the molecular features to an isotope group characterized by a chemical formula and an isotope distribution. The analysis unit can also retention time and accurate mass-align the spectrometry files, at the level of individual features within isotope envelopes using a proprietary alignment algorithm and searched against human reference protein database (Uniprot human ref 20150303.fasta via Comet) using a 10 parts per million peptide precursor mass tolerance.

In some embodiments, the analysis unit is configured to rank the statistically significant molecular features using statistical and practical filtering. In some embodiments, the statistical filtering can include t-tests. Other methods of statistical filtering are well-known in the art.

In some embodiments, the practical filtering conducted by the analysis unit can include excluding any statistically significant molecular features that are not present in at least two-thirds of the samples contacted with the ligand. In some embodiments, the practical filtering comprises excluding any statistically significant molecular features that were the only significant features in a single isotope group with a p value of less than about 0.01 based on the statistical filtering.

In some embodiments, the statistically significant molecular features that are determined to still be significant based upon the statistical and practical filtering are highly ranked by the analysis unit. For example, a significance threshold can be set. The analysis unit can compare the molecular features to the significance threshold to determine where the molecular features are significant following the statistical and practical filtering.

In some embodiments, the amino acid sequences of the statistically significant molecular features are identified using processes well-known in the art. Such processes include, but are not limited to, peptide mass fingerprinting and data-dependent MS/MS acquisition followed by a computational search against an in silico digest of the proteome. In some embodiments, the process includes data-dependent MS/MS acquisition followed by a computational search against an in silico digest of the proteome.

The statistically significant molecular features may be a part of a protein capable of binding the ligand. Thus, in some embodiments, identifying the protein that is capable of binding the ligand comprises comparing the amino acid sequences of the statistically significant molecular features with a protein database and identifying which proteins of the protein database contain the statistically significant molecular features. In some embodiments, the statistically significant molecular features that may be a part of a protein capable of binding the ligand include the highly ranked statistically significant molecular features.

The similarity between amino acid sequences is expressed in terms of the similarity between the sequences, otherwise referred to as sequence identity. Sequence identity is frequently measured in terms of percentage identity (or similarity or homology); the higher the percentage, the more similar the two sequences are. Homologs or variants of a polypeptide will possess a relatively high degree of sequence identity when aligned using standard methods.

Methods of alignment of sequences for comparison are well known in the art. Various programs and alignment algorithms are described in: Smith and Waterman, *Adv. Appl. Math.* 2:482, 1981; Needleman and Wunsch, *J. Mol. Biol.* 48:443, 1970; Pearson and Lipman, *Proc. Natl. Acad. Sci. U.S.A.* 85:2444, 1988; Higgins and Sharp, Gene 73:237, 1988; Higgins and Sharp, CABIOS 5:151, 1989; Corpet et al., *Nucleic Acids Research* 16:10881, 1988; and Pearson and Lipman, *Proc. Natl. Acad. Sci. U.S.A.* 85:2444, 1988. Altschul et al., *Nature Genet.* 6:119, 1994, presents a detailed consideration of sequence alignment methods and homology calculations.

The NCBI Basic Local Alignment Search Tool (BLAST) (Altschul et al., *J. Mol. Biol.* 215:403, 1990) is available from several sources, including the National Center for Biotechnology Information (NCBI, Bethesda, Md.) and on the internet, for use in connection with the sequence analysis programs blastp, blastn, blastx, tblastn and tblastx. A description of how to determine sequence identity using this program is available on the NCBI website on the internet.

Homologs and variants of a protein are typically characterized by possession of at least about 75%, for example at least about 80%, about 90%, about 95%, about 96%, about 97%, about 98% or 99% sequence identity counted over the full length alignment with the amino acid sequence of the antibody using the NCBI Blast 2.0, gapped blastp set to default parameters. For comparisons of amino acid sequences of greater than about 30 amino acids, the Blast 2 sequences function is employed using the default BLOSUM62 matrix set to default parameters, (gap existence cost of 11, and a per residue gap cost of 1). When aligning short peptides (fewer than around 30 amino acids), the alignment should be performed using the Blast 2 sequences function, employing the PAM30 matrix set to default parameters (open gap 9, extension gap 1 penalties). Proteins with even greater similarity to the reference sequences will show increasing percentage identities when assessed by this method, such as at least 80%, at least 85%, at least 90%, at least 95%, at least 98%, or at least 99% sequence identity. When less than the entire sequence is being compared for sequence identity, homologs and variants will typically possess at least 80% sequence identity over short windows of 10-20 amino acids, and may possess sequence identities of at least 85% or at least 90% or 95% depending on their similarity to the reference sequence. Methods for determining sequence identity over such short windows are available at the NCBI website on the internet. One of skill in the art will appreciate that these sequence identity ranges are provided for guidance only; it is entirely possible that strongly significant homologs could be obtained that fall outside of the ranges provided.

Computer Apparatus and Processing

The above-described embodiments can be implemented in any of numerous ways. For example, the embodiments may be implemented using hardware, software or a combination thereof. When implemented in software, the software code can be executed on any suitable processor or collection of processors, whether provided in a single computer or distributed among multiple computers.

Also, a computer may have one or more input and output devices. These devices can be used, among other things, to present a user interface. Examples of output devices that can be used to provide a user interface include printers or display screens for visual presentation of output and speakers or other sound generating devices for audible presentation of output. Examples of input devices that can be used for a user interface include keyboards, and pointing devices, such as mice, touch pads, and digitizing tablets. As another example, a computer may receive input information through speech recognition or in other audible format.

Such computers may be interconnected by one or more networks in any suitable form, including a local area network or a wide area network, such as an enterprise network, an intelligent network (IN) or the Internet. Such networks may be based on any suitable technology and may operate according to any suitable protocol and may include wireless networks, wired networks or fiber optic networks.

A computer employed to implement at least a portion of the functionality described herein may comprise a memory, one or more processing units (also referred to herein simply as "processors"), one or more communication interfaces, one or more display units, and one or more user input devices. The memory may comprise any computer-readable media, and may store computer instructions (also referred to herein as "processor-executable instructions") for implementing the various functionalities described herein. The processing unit(s) may be used to execute the instructions. The communication interface(s) may be coupled to a wired or wireless network, bus, or other communication means and may therefore allow the computer to transmit communications to and/or receive communications from other devices. The display unit(s) may be provided, for example, to allow a user to view various information in connection with execution of the instructions. The user input device(s) may be provided, for example, to allow the user to make manual adjustments, make selections, enter data or various other information, and/or interact in any of a variety of manners with the processor during execution of the instructions.

The various methods or processes outlined herein may be coded as software that is executable on one or more processors that employ any one of a variety of operating systems or platforms. Additionally, such software may be written using any of a number of suitable programming languages and/or programming or scripting tools, and also may be compiled as executable machine language code or intermediate code that is executed on a framework or virtual machine.

In this respect, various inventive concepts may be embodied as a computer readable storage medium (or multiple computer readable storage media) (e.g., a computer memory, one or more floppy discs, compact discs, optical discs, magnetic tapes, flash memories, circuit configurations in Field Programmable Gate Arrays or other semiconductor devices, or other non-transitory medium or tangible computer storage medium) encoded with one or more programs that, when executed on one or more computers or other processors, perform methods that implement the various embodiments of the invention discussed above. The computer readable medium or media can be transportable, such that the program or programs stored thereon can be loaded onto one or more different computers or other processors to implement various aspects of the present invention as discussed above.

The terms "program" or "software" are used herein in a generic sense to refer to any type of computer code or set of computer-executable instructions that can be employed to program a computer or other processor to implement various aspects of embodiments as discussed above. Additionally, it should be appreciated that according to one aspect, one or more computer programs that when executed perform methods of the present invention need not reside on a single computer or processor, but may be distributed in a modular fashion amongst a number of different computers or processors to implement various aspects of the present invention.

Computer-executable instructions may be in many forms, such as program modules, executed by one or more computers or other devices. Generally, program modules include routines, programs, objects, components, data structures, etc. that perform particular tasks or implement particular abstract data types. Typically the functionality of the program modules may be combined or distributed as desired in various embodiments.

Also, data structures may be stored in computer-readable media in any suitable form. For simplicity of illustration, data structures may be shown to have fields that are related through location in the data structure. Such relationships may likewise be achieved by assigning storage for the fields with locations in a computer-readable medium that conveys relationship between the fields. However, any suitable mechanism may be used to establish a relationship between information in fields of a data structure, including through the use of pointers, tags or other mechanisms that establish relationship between data elements.

Also, various inventive concepts may be embodied as one or more methods, of which an example has been provided. The acts performed as part of the method may be ordered in any suitable way. Accordingly, embodiments may be constructed in which acts are performed in an order different than illustrated, which may include performing some acts simultaneously, even though shown as sequential acts in illustrative embodiments.

II. Definitions

As used herein, the term "about" will be understood by persons of ordinary skill in the art and will vary to some extent depending upon the context in which it is used. If there are uses of the term which are not clear to persons of ordinary skill in the art given the context in which it is used, "about" will mean up to plus or minus 10% of the particular term.

Certain ranges are presented herein with numerical values being preceded by the term "about". The term "about" is used herein to provide literal support for the exact number that it precedes, as well as a number that is near to or approximately the number that the term precedes. In determining whether a number is near to or approximately a specifically recited number, the near or approximating unrecited number may be a number which, in the context in which it is presented, provides the substantial equivalent of the specifically recited number.

As used herein, an "isolated" biological component (such as a nucleic acid, peptide or protein) has been substantially separated, produced apart from, or purified away from other biological components in the cell of the organism in which the component naturally occurs, i.e., other chromosomal and extrachromosomal DNA and RNA, and proteins. Nucleic acids, peptides and proteins which have been "isolated" thus include nucleic acids and proteins purified by standard purification methods. The term also embraces nucleic acids, peptides and proteins prepared by recombinant expression in a host cell as well as chemically synthesized nucleic acids. An isolated cell type has been substantially separated from other cell types, such as a different cell type that occurs in an organ. A purified cell or component can be at least 90%, at least 95%, at least 96%, at least 97%, at least 98%, or at least 99% pure.

As used herein, the term "protein" (also equivalent to a "polypeptide") refers to a polymer in which the monomers are amino acid residues that are joined together through amide bonds. When the amino acids are alpha-amino acids, either the L-optical isomer or the D-optical isomer can be used, the L-isomers being preferred. The terms "polypeptide" or "protein" as used herein is intended to encompass any amino acid sequence and include modified sequences such as glycoproteins. The term terms "polypeptide" or "protein" is specifically intended to cover naturally occurring proteins, as well as those that are recombinantly or synthetically produced.

The term "soluble" refers to a form of a protein or polypeptide that is not inserted into a cell membrane or a form of a protein or polypeptide that remains in solution. In some embodiments, a form of a protein or polypeptide that remains in solution has not precipitated out of the solution.

As used herein, the term "ligand" refers to a small molecule that binds to a larger molecule. In some embodiments, a ligand includes a small molecule pharmaceutical drug.

As used herein, the term "statistically significant" refers to the likelihood that a relationship between two or more variables is caused by something other than random chance. A statistically significant result is achieved when a p-value is less than the significance level (a). In some embodiments, a statistically significant molecular feature refers to a molecular feature that exhibits a statistically significant difference in quantity between the samples contacted with a ligand and a sample that is not contacted with a ligand. In some embodiments, a statistically significant molecular feature is a molecular feature whose increase in quantity in the samples contacted with the ligand compared to the sample not contacted with the ligand is caused by something other than random chance. In some embodiments, a statistically significant molecular feature is a molecular feature whose decrease in quantity in the samples contacted with the ligand compared to the sample not contacted with the ligand is caused by something other than random chance.

As used herein, "CHORUS" refers to a web application available online at https://chorusproject.org which allows for the storing, sharing, visualizing, and analyzing of spectrometry files.

Unless otherwise explained, all technical and scientific terms used herein have the same meaning as commonly understood by one of ordinary skill in the art to which this disclosure belongs.

It is further to be understood that all base sizes or amino acid sizes, and all molecular weight or molecular mass values, given for nucleic acids or polypeptides are approximate, and are provided for description. Although methods and materials similar or equivalent to those described herein can be used in the practice or testing of this disclosure, suitable methods and materials are described below.

The term "comprises" means "includes."

All publications, patent applications, patents, and other references mentioned herein are incorporated by reference in their entirety. In case of conflict, the present specification, including explanations of terms, will control. In addition, the materials, methods, and examples are illustrative only and not intended to be limiting.

It is noted that, as used herein and in the appended claims, the singular forms "a", "an", and "the" include plural referents unless the context clearly dictates otherwise. It is further noted that the claims may be drafted to exclude any optional element. As such, this statement is intended to serve as antecedent basis for use of such exclusive terminology as "solely", "only" and the like in connection with the recitation of claim elements, or use of a "negative" limitation. Similarly, the word "or" is intended to include "and" unless the context clearly indicates otherwise.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, representative illustrative methods and materials are now described. Definitions of common terms in molecular biology may be found in Benjamin Lewin, *Genes V*, published by Oxford University Press, 1994 (ISBN 0-19-854287-9); Kendrew et al. (eds.), *The Encyclopedia of Molecular Biology*, published by Blackwell Science Ltd., 1994 (ISBN 0-632-02182-9); and Robert A. Meyers (ed.), *Molecular Biology and Biotechnology: a Comprehensive Desk Reference*, published by VCH Publishers, Inc., 1995 (ISBN 1-56081-569-8).

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges and are also encompassed within the invention, subject to any specifically excluded limit in the stated range. Where the stated range includes one or both of the limits, ranges excluding either or both of those included limits are also included in the invention.

This disclosure is not limited to particular embodiments described, as such may, of course, vary. It is also to be understood that the terminology used herein is for the purpose of describing particular embodiments only, and is not intended to be limiting, since the scope of the present invention will be limited only by the appended claims.

As will be apparent to those of skill in the art upon reading this disclosure, each of the individual embodiments described and illustrated herein has discrete components and features which may be readily separated from or combined with the features of any of the other several embodiments without departing from the scope or spirit of the present invention. Any recited method can be carried out in the order of events recited or in any other order which is logically possible.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present invention is not entitled to antedate such publication by virtue of prior invention. Further, the dates of publication provided may be different from the actual publication dates which may need to be independently confirmed.

III. Working Examples

The present technology is further illustrated by the following examples, which should not be construed as limiting in any way.

The examples described herein exemplify the use of DISRUPT to identify protein targets of staurosporine and mdivi-1, an investigational compound with unknown oncologic activity. The examples described herein demonstrate that top ranked features associate with canonical targets for staurosporine and DPP3 for mdivi-1.

Identification and Ranking of Proteins that Bind Staurosporine

To test the ability of the DISRUPT platform to identify canonical targets of the well characterized small molecule drug, staurosporine, K562 cells, a human bone marrow chronic myelogenous leukemia cell line, were treated with 2 µM staurosporine, an exhaustively described kinase inhibitor that binds competitively to ATP binding sites as shown in FIG. 1. Samples were heated to 56° C. for ten minutes to stimulate protein agglutination (protein clumping) and agglutinated proteins were removed from solution by centrifugation at 20,000 g.

Figure 2:
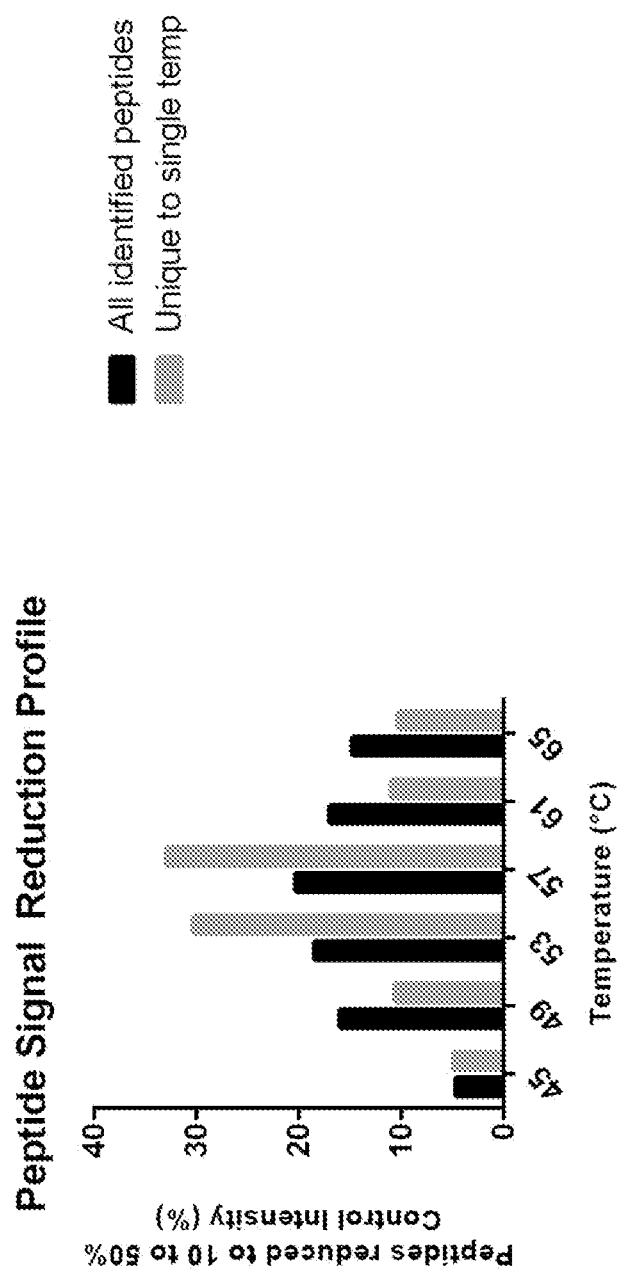
FIG. 2 is a graphical illustration of the denaturation curves of all proteins in a K562 lysate. Lysates were heated to various temperatures across the denaturation curve. The reduction of intensity was calculated at the feature level for all identified peptides, and the number of peptides whose protein intensities decreased by 50-90% were calculated. The number of peptides in this range was calculated for peptides that were in this range at multiple temperatures and at a single temperature, and the data was plotted. It was determined that a temperature of 56° C. would have the greatest information content for the largest subset of proteins.

Ligand binding thermally stabilized proteins, resulting in increased solubility relative to unbound protein in higher temperatures. This single temperature of 56° C. was selected for the experiment due to its central location in the denaturation curve of the highest number of proteins, as shown in FIG. 2. Proteins that did not interact with staurosporine agglutinated and were removed from solution in equal amounts.

To measure the relative abundance of proteins in solution, lysates were subjected to tryptic digestion, desalting and quantitative proteomic analysis. Peptide samples were separated by reversed phase C18 nanoflow liquid chromatography (nLC), ionized by electrospray ionization, and analyzed with a hybrid ion trap/high-resolution Fourier transform mass spectrometer. High-resolution full scan mass spectra (MS) were acquired at a frequency of approximately 1 Hz while low-resolution tandem mass spectra (MS/MS) were acquired at a rate of 3 Hz for precursor ions that exceed an intensity threshold. To enhance the quantification of the vast number of molecular features present in high-resolution data, the acquisition of full-scan MS spectra were prioritized over the collection of MS/MS spectra that are used for peptide identification, resulting in approximately 10 quantitative measurements per chromatographic peak.

Samples were analyzed in a balanced run order to compensate for drifts in mass spectrometry response that occurs as a function of time. Each sample was analyzed once and the resulting data file was uploaded to a cloud-based data analysis platform, CHORUS (www.chorusproject.org), that was developed to support the efficient analysis of high-resolution mass spectrometry data. Label-free differential mass spectrometry (dMS) was used to quantify hundreds of thousands of features detected by nLC-MS analysis.

Combinations of statistical and practical filters were used to select and prioritize specific features for identification by nLC-MS/MS. A key attribute of the DISRUPT platform that distinguishes it from all other previous CETSA type experiments is that this approach scores for significant features without the use of curve fitting or a priori knowledge. It is unbiased and not reliant on errors and limitations associated with strategies that emphasize the acquisitions of large number of MS/MS spectra and the time-consuming and error-prone steps associated with peptide identification and the reconstruction of protein level quantification results.

Figure 3:
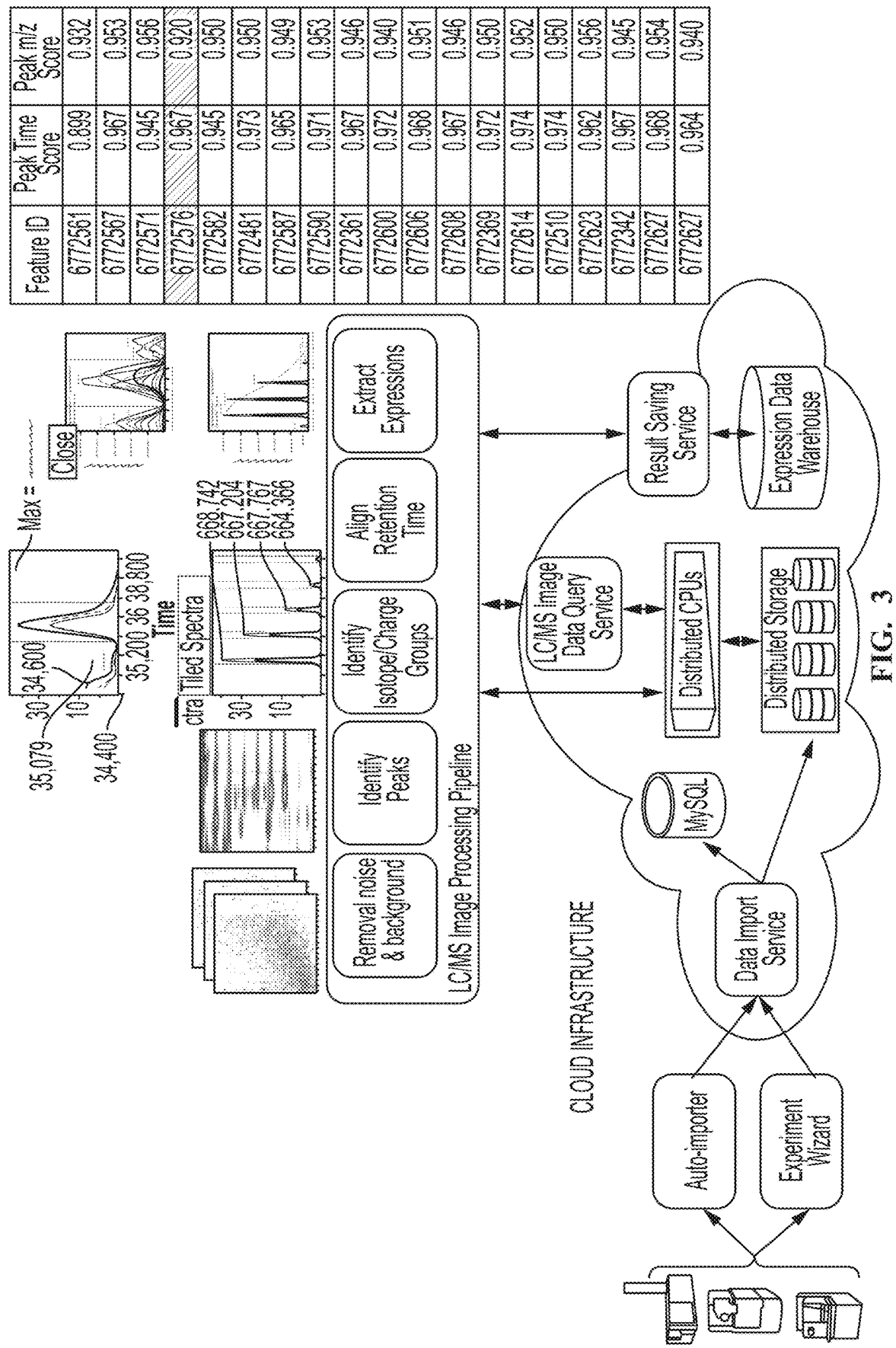
FIG. 3 is a schematic illustration of the major data types, computational steps, and cloud-computing platform that facilitates the label-free differential mass spectrometry (dMS) data analysis. The differential mass spectrometry data analysis workflow has been integrated into a single cloud based platform that supports the efficient and scalable analysis of high-resolution LC-MS data.
Figure 6A:
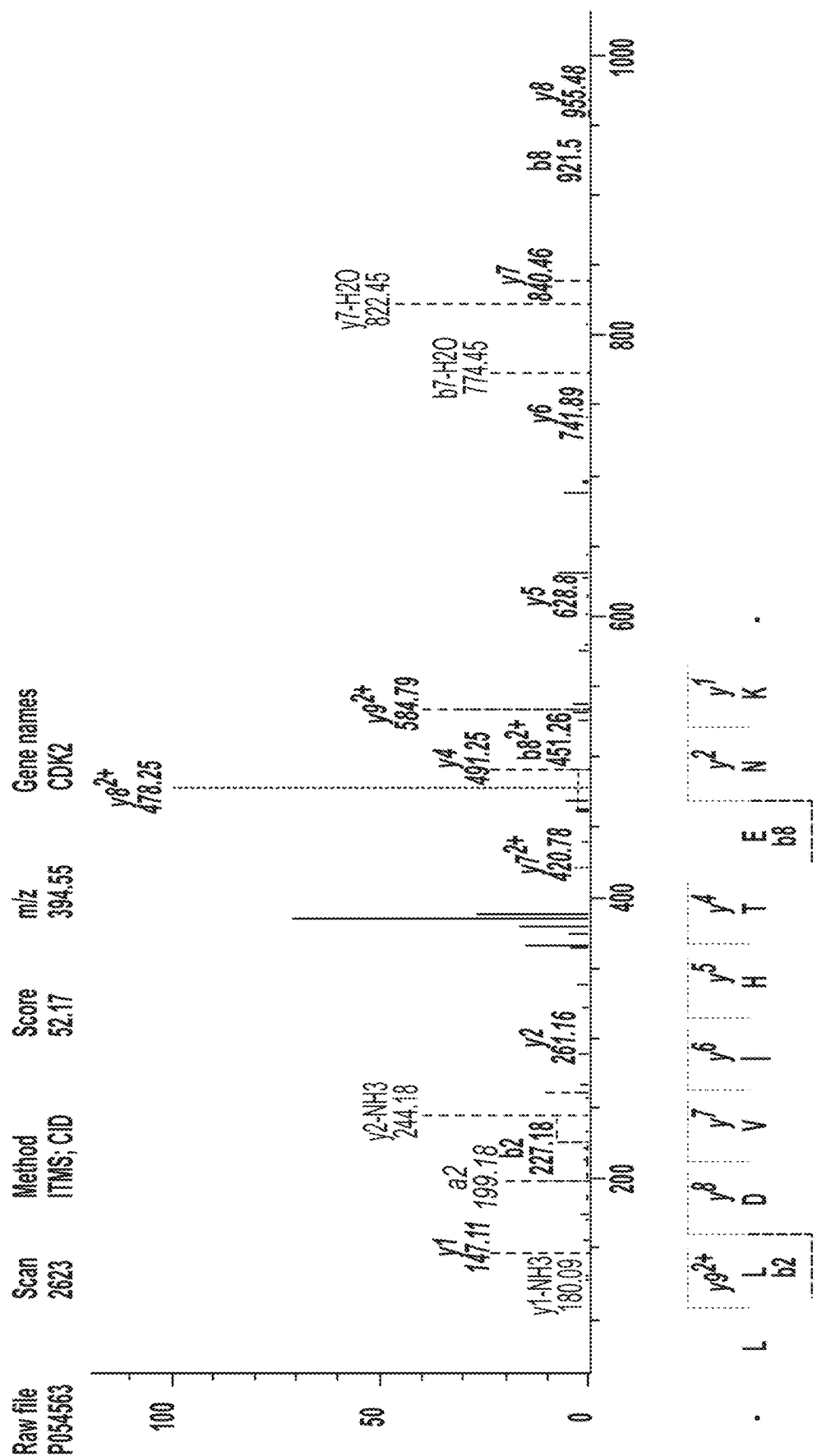
FIGS. 6A-G represent annotated mass spectra for identified features with p<0.0001 from the lysates treated with staurosporine.
Figure 6B:
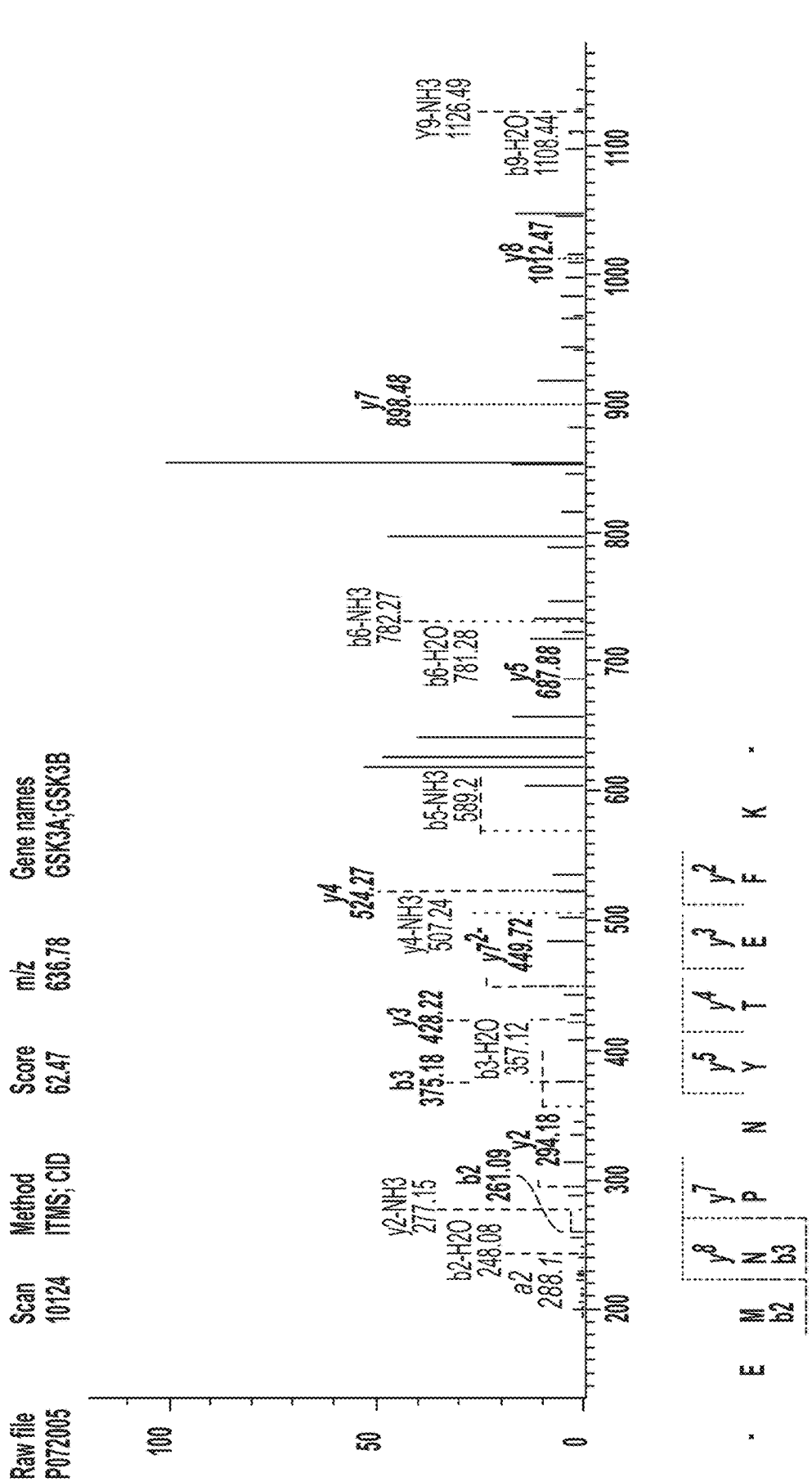
Figure 6C:
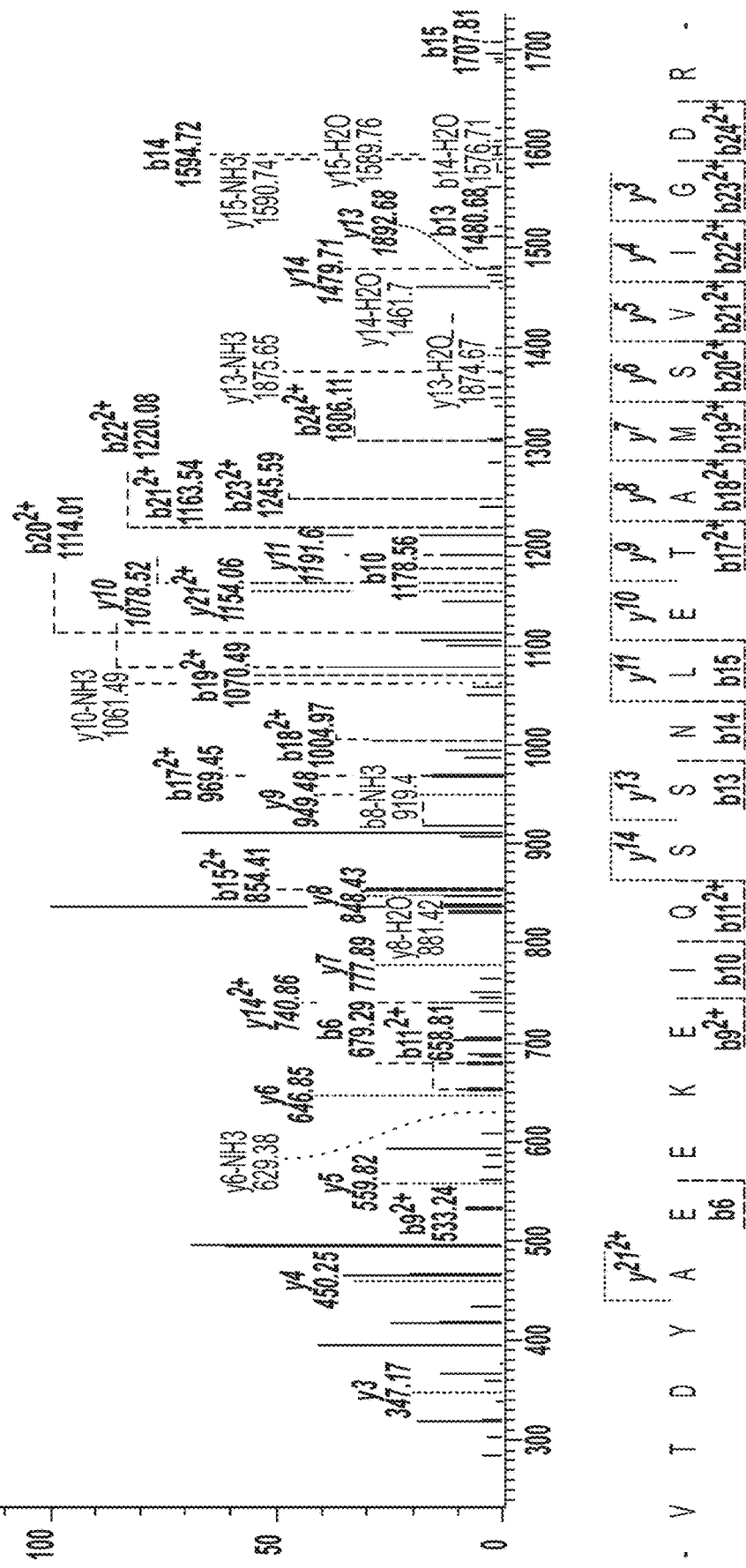
Figure 6D:
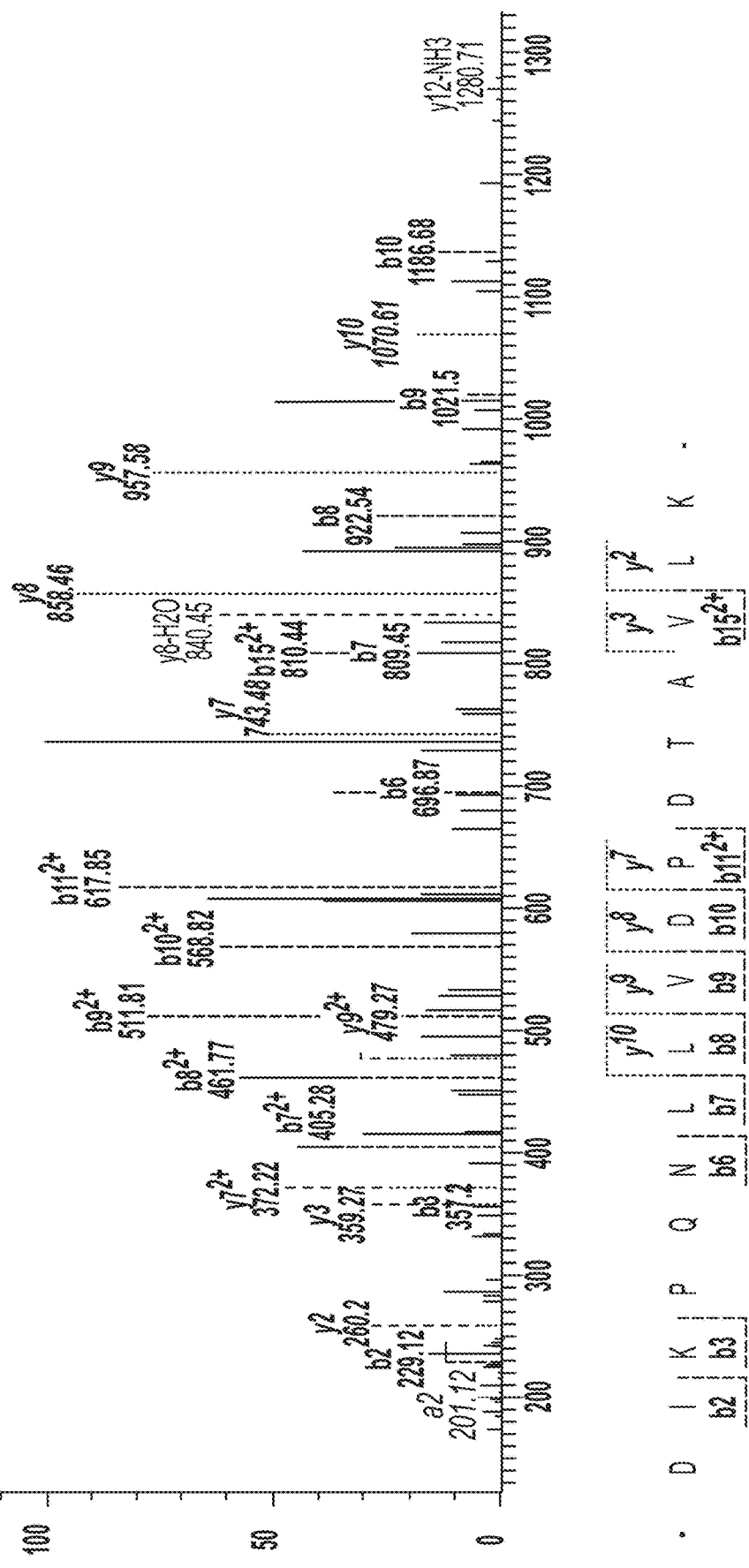
Figure 6E:
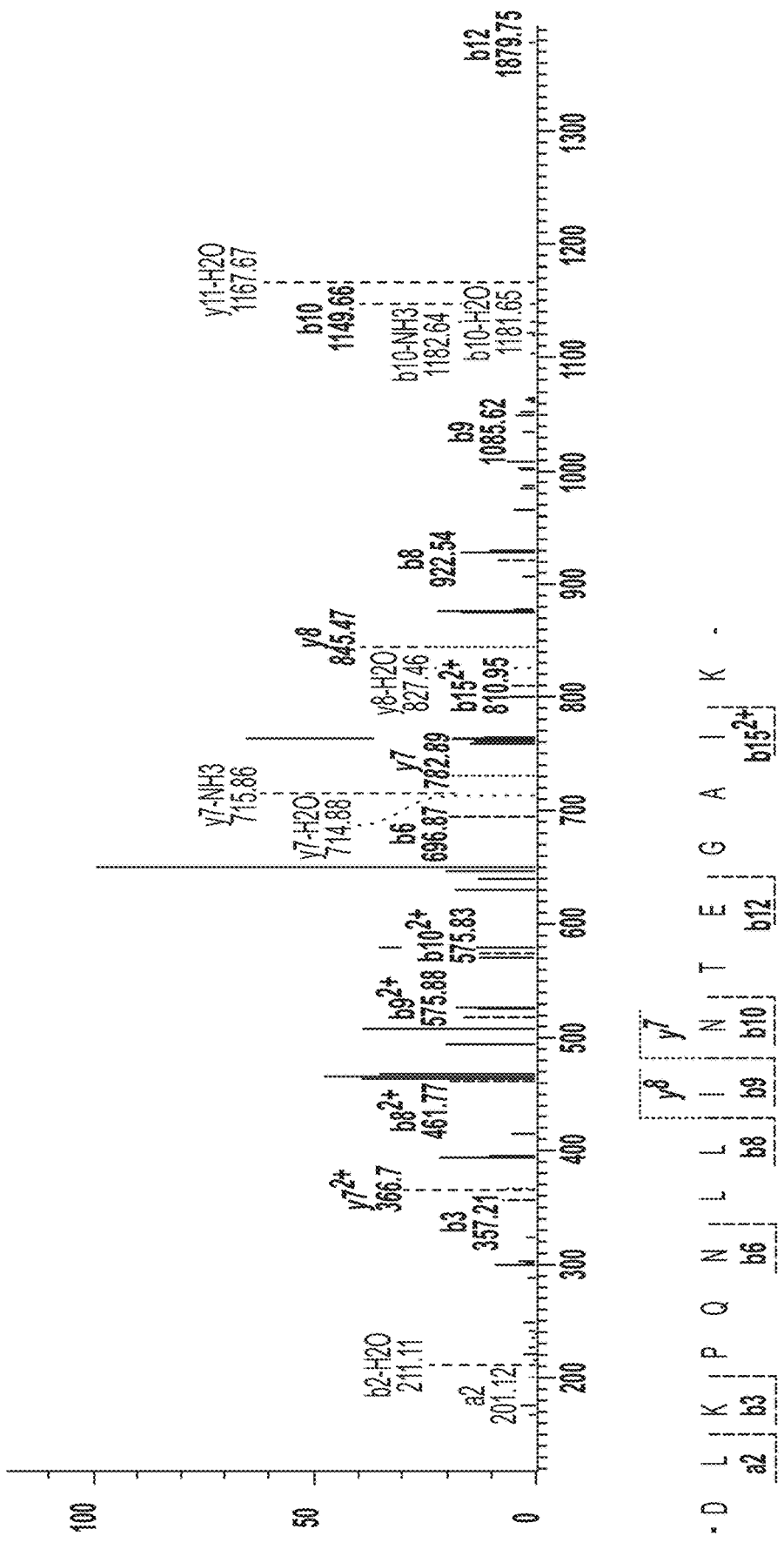
Figure 6F:
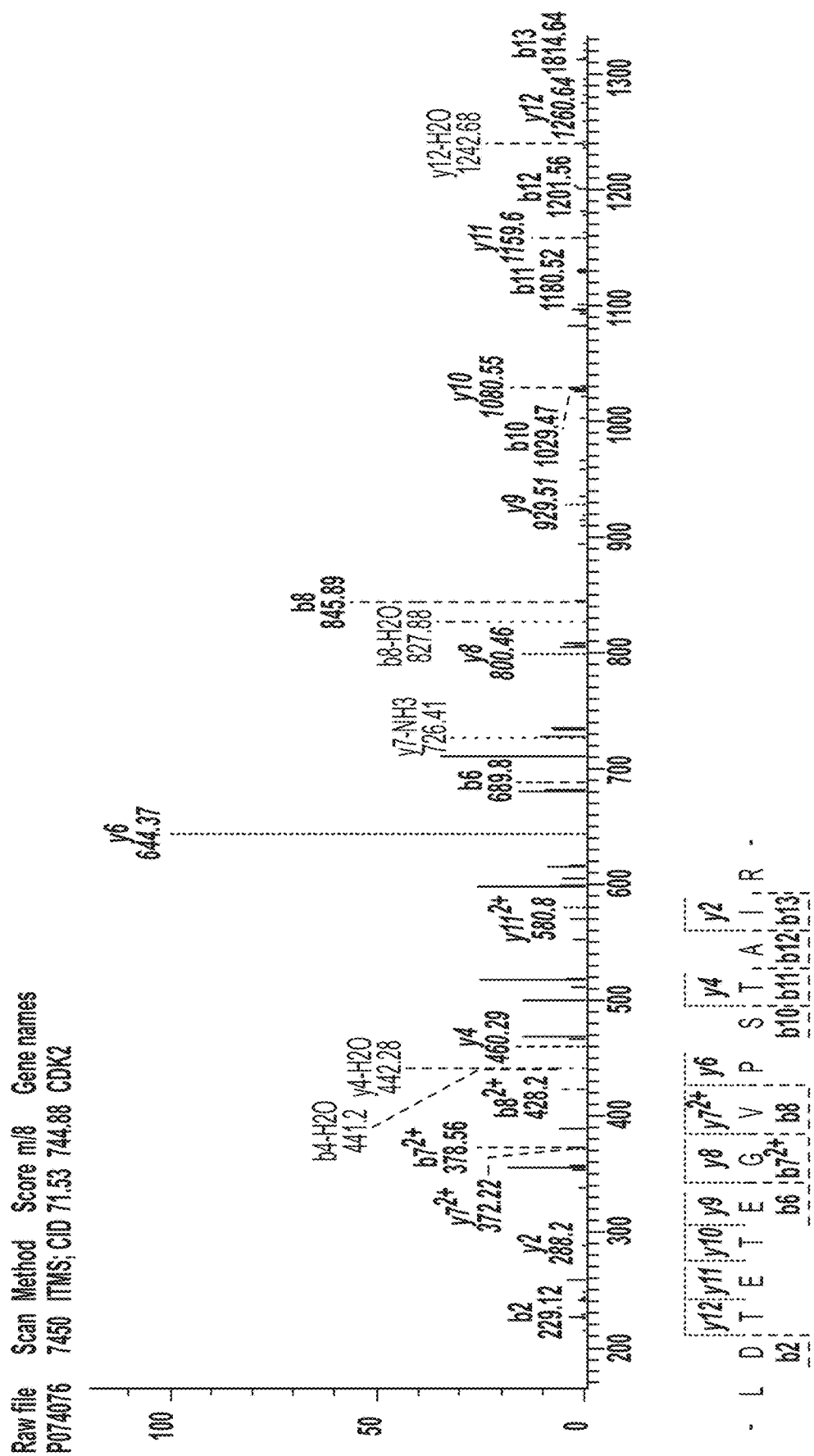
Figure 6G:
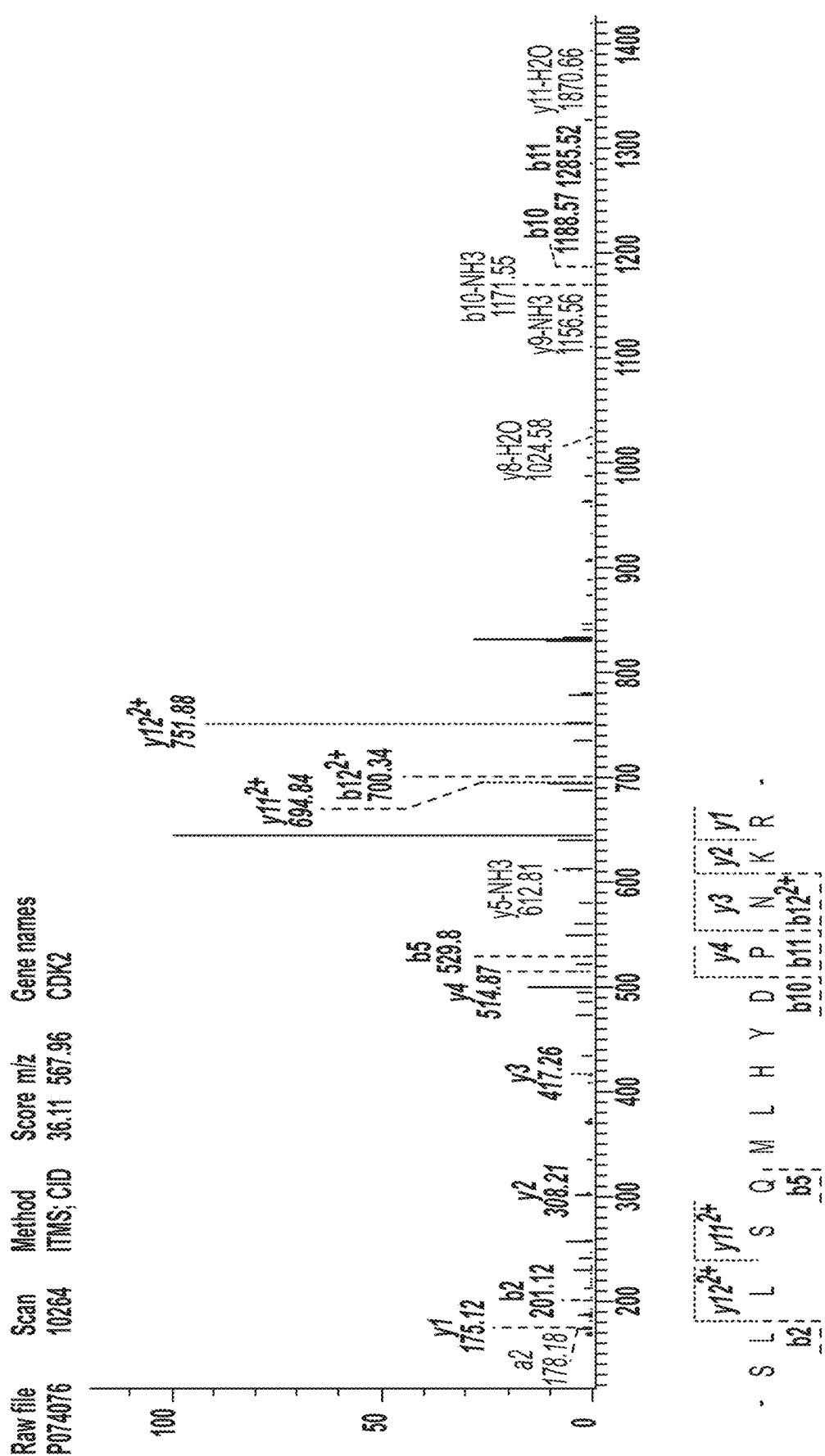
Figure 8A:
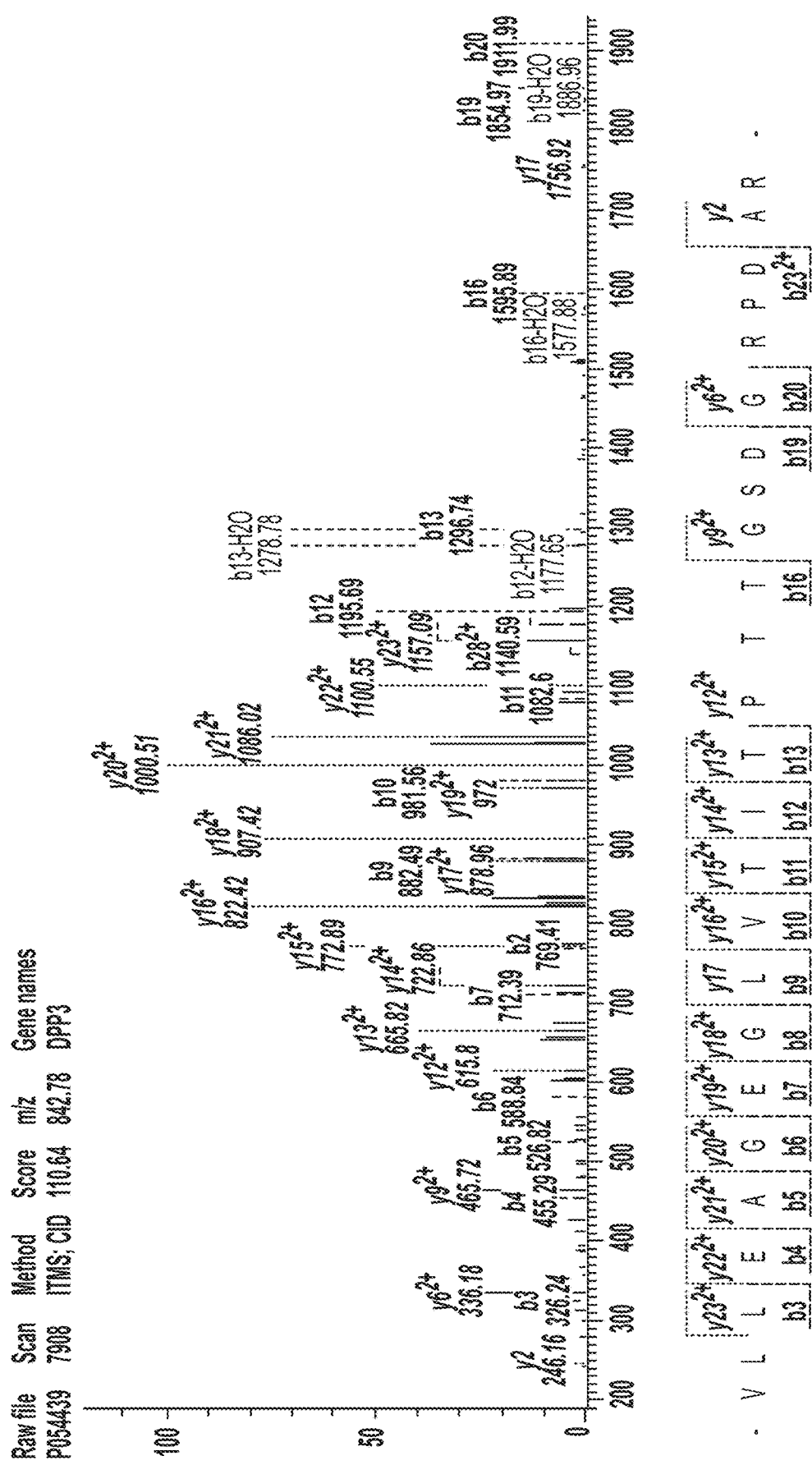
FIGS. 8A-G represent annotated mass spectra for identified features with p<0.0001 from the cancer cells treated with mdivi-1.
Figure 8B:
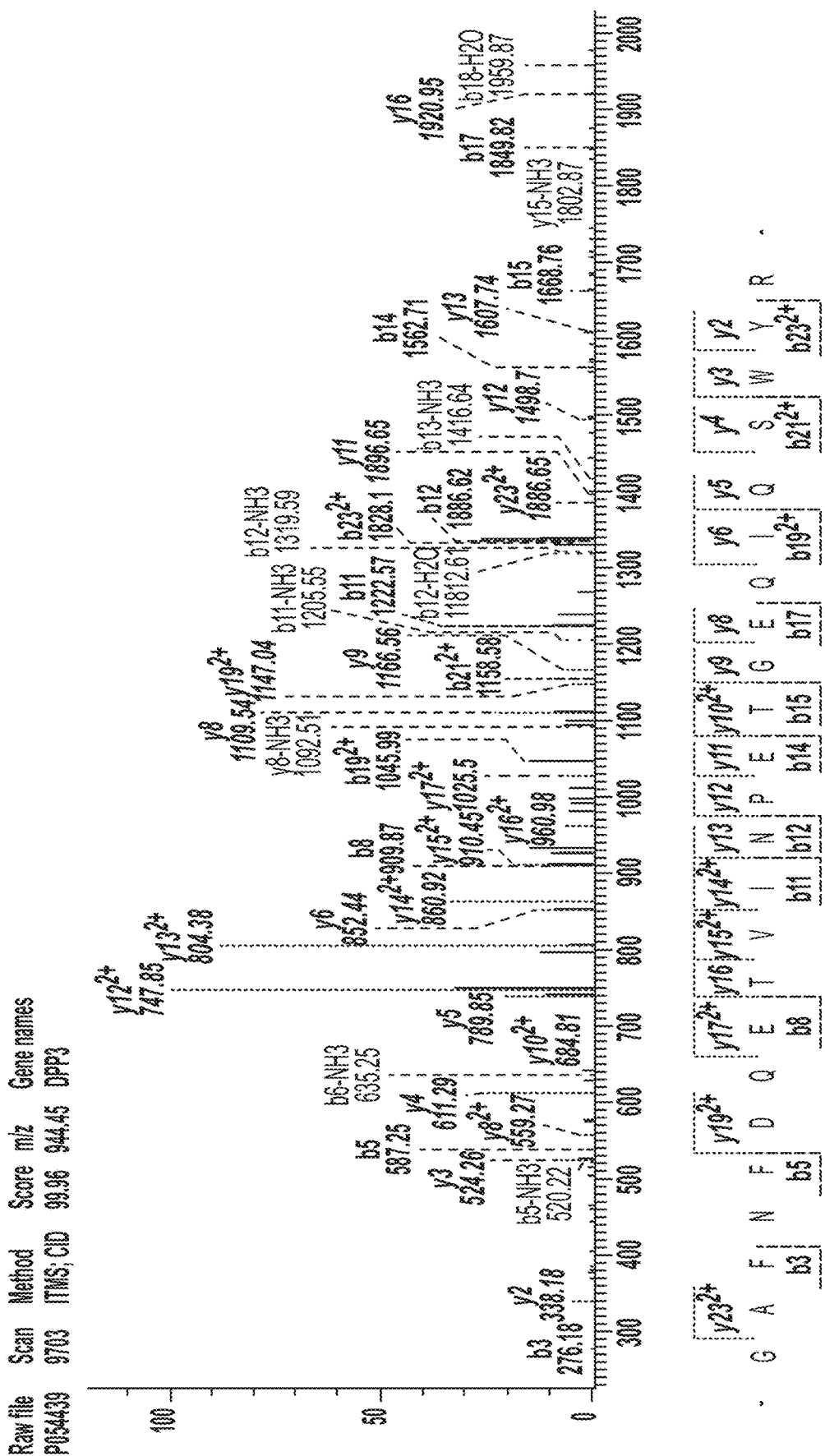
Figure 8C:
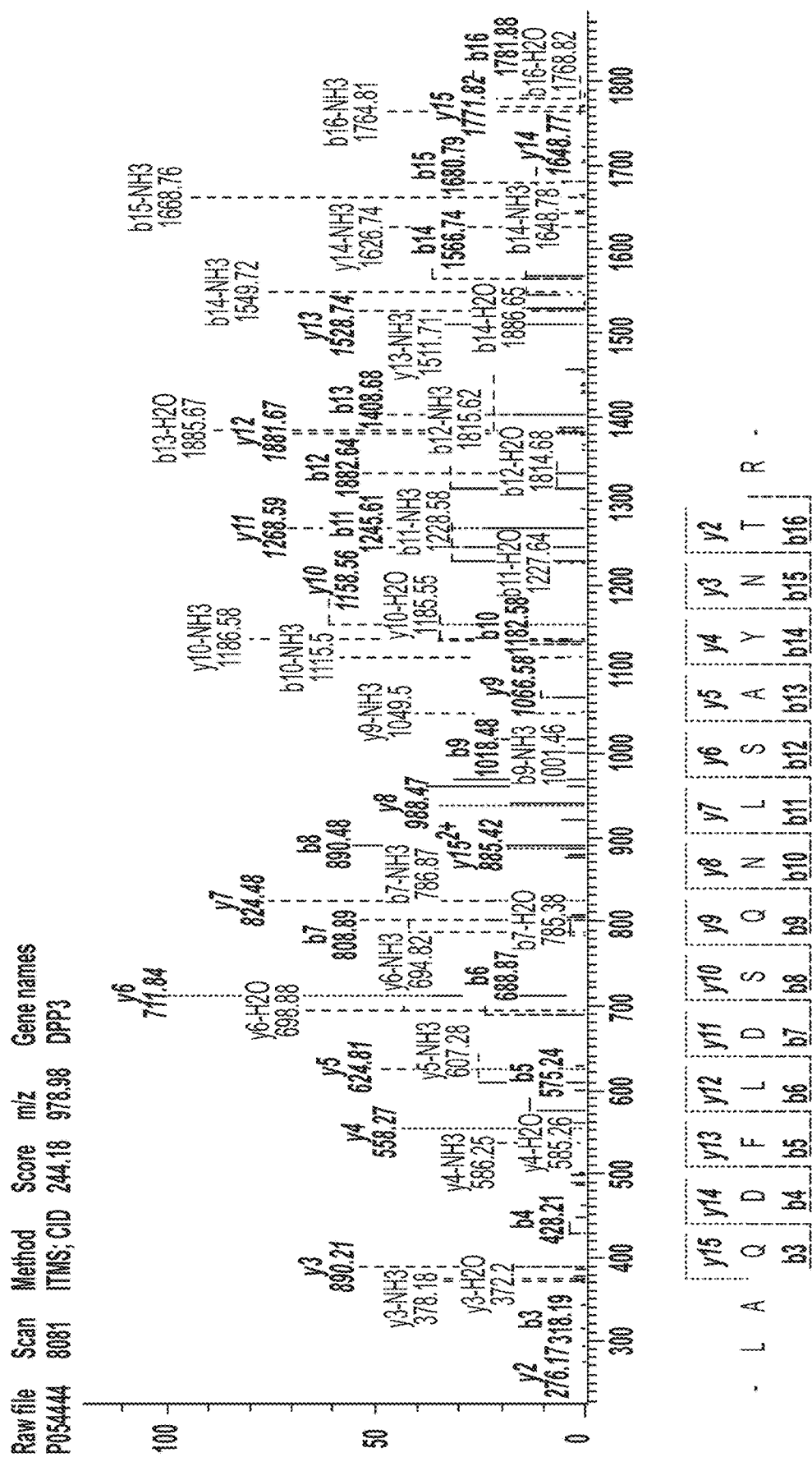
Figure 8D:
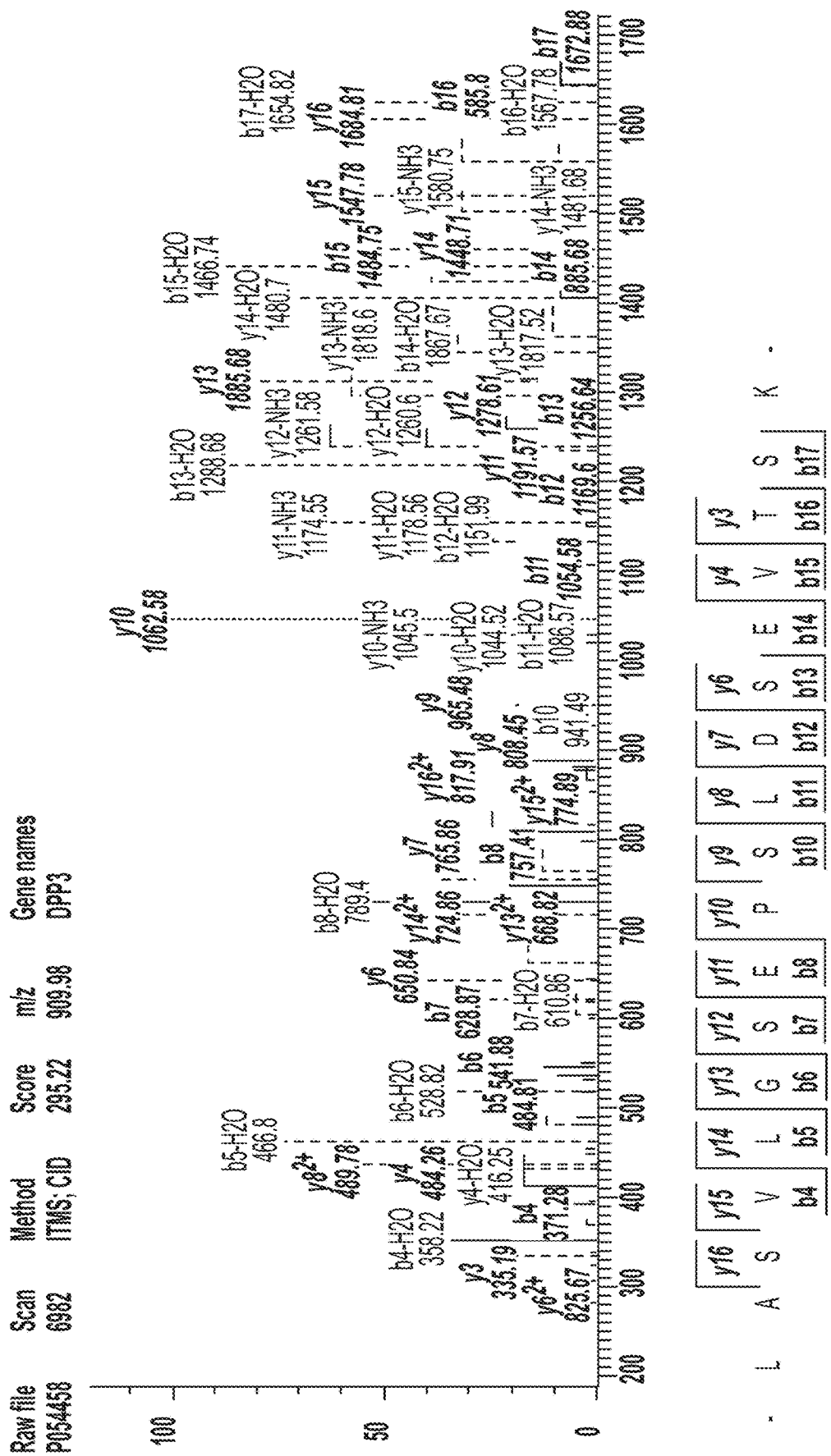
Figure 8E:
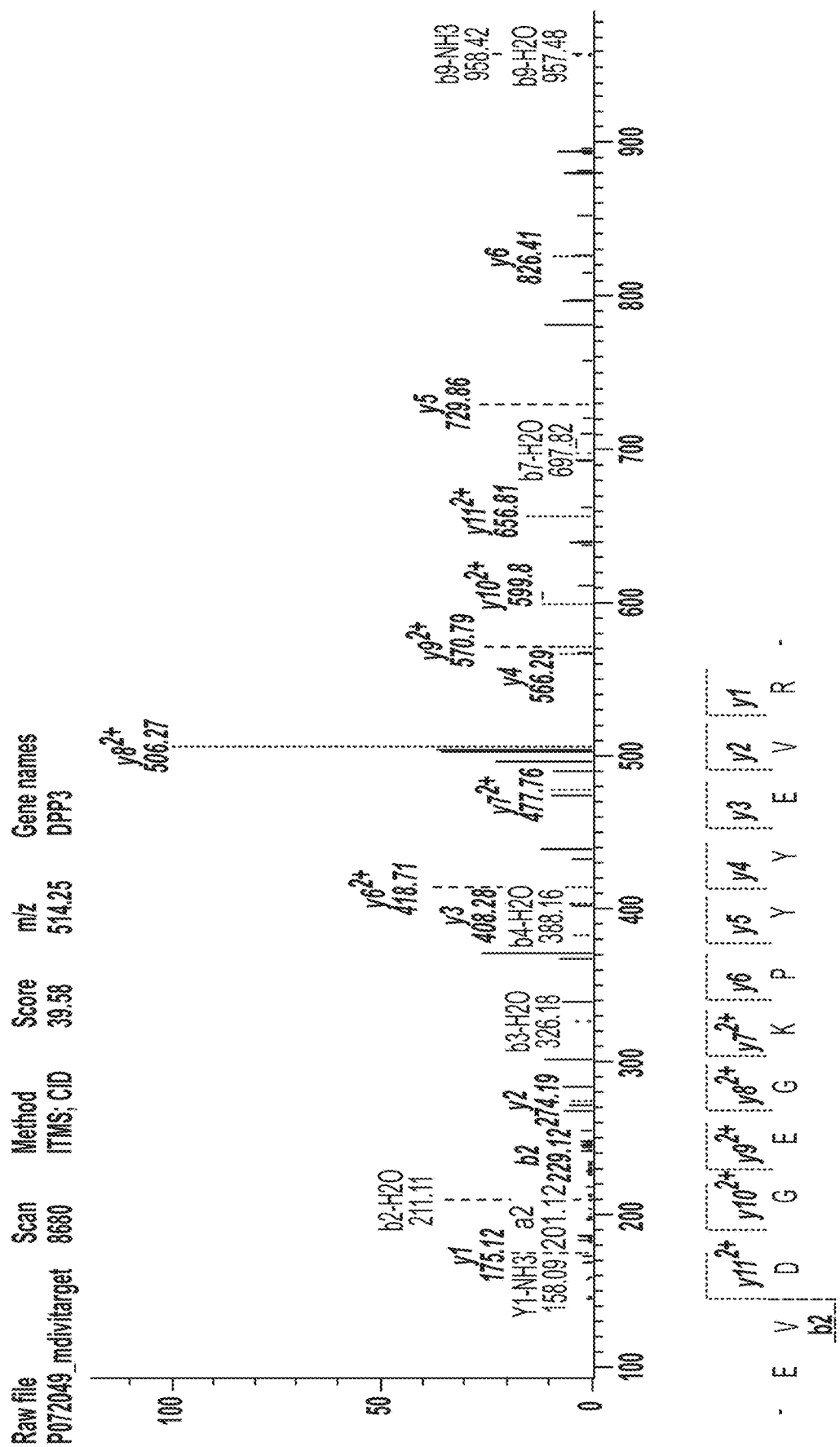
Figure 8F:
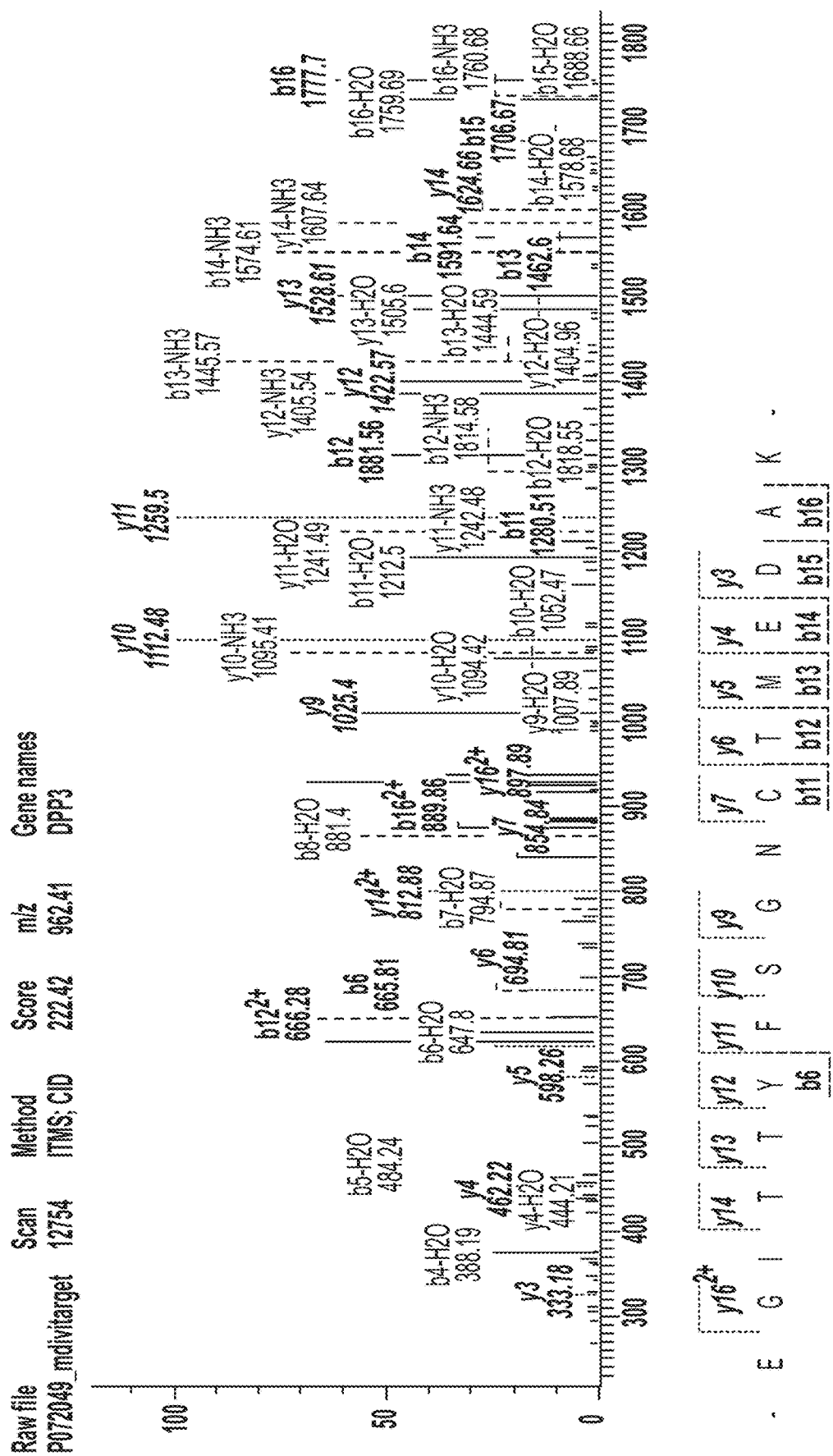
Figure 8G:
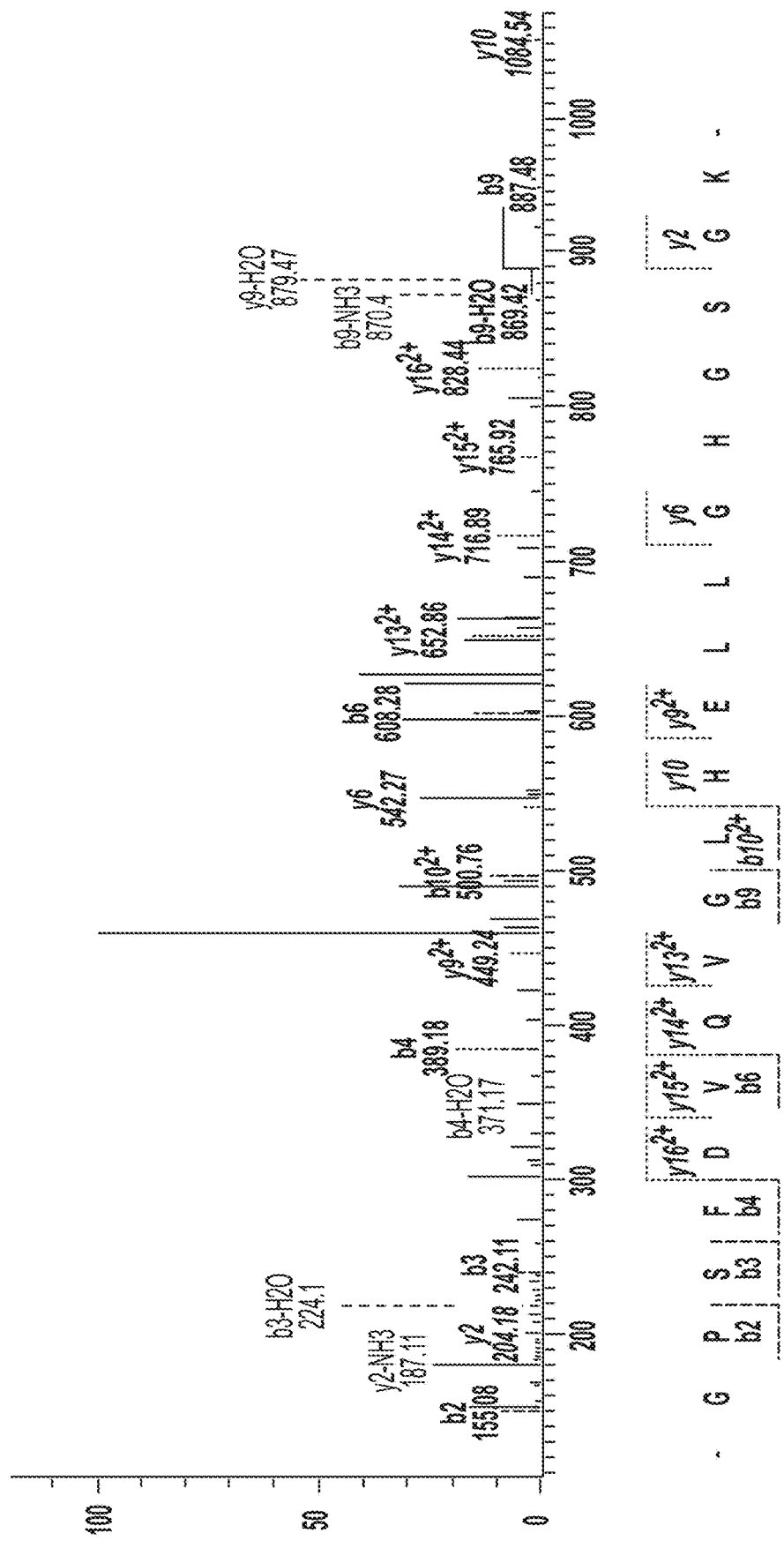

FIG. 3 outlines the major computational steps in the dMS workflow. One or more computational steps of the dMS workflow can be performed from the above described analysis unit. A key attribute of the DISRUPT platform is the analysis of large volumes of nLC-MS data, without common data reductions steps that limit analyses to identified peptides or isotopic labels. An image processing service removed noise and performed peak detection to produce a list of features that are defined by an accurate mass-to-charge ratio, retention time, and relative intensity. Next, the isotope grouping (IG) service assigned features to isotope groups that share a common chemical formula and isotope distribution. The merge across file service, aligns and extracts expression data for each feature from all of the samples were analyzed in an experiment. Next, MS/MS spectra were matched to features based on retention time and accurate m/z, and searched against a reference protein database to yield peptide and protein identification assignment. The cloud-based implementation of dMS provided the massive scalability that supports the analysis of large data cubes containing tens to hundreds of samples.

To demonstrate that CHORUS is able to successfully align and quantify features across multiple nLC-MS samples, 14 technical replicates of a K562 digest were analyzed serially and 492,835 features were aligned and quantified. Twenty features with intensities nearest to $2\times10^{13}$, $1\times10^{13}$, $8\times10^{12}$, ... $2\times10^{9}$ counts, were selected coefficients of variance (CV) were calculated as shown in FIG. 4. The range of CV measurements for the 20 features was 8-18% with an average of 13%. Similar CV measurements were observed for signals that cover an intensity range spanning four orders of magnitude, indicating that both low and high abundance features were measured with similar precision. The features were also quantified using manual peak selection tools in the Thermo XCalibur software suite. These measurements yielded an average coefficient of variance of 12%, with a range of 5-26%.

A dMS comparison of 10 staurosporine treated K652 lysates and 10 controls detected 270,822 features that were associated with 108,594 isotope groups. Of these, 23,211 features were annotated with 4,394 peptide sequences from 703 protein sequences. Features that exhibit a statistically significant difference in relative abundance between the treated and untreated samples were ranked using a combination of statistical and practical filters. First, a practical filter that requires a non-zero intensity value in at least six of ten samples was used to select 200,256 features. Next, a two tailed unpaired equal variance Student's t-test was applied, and the fold change between drug treated and vehicle samples were calculated, as shown in FIG. 5A. A practical filter was applied to exclude significant features that were the only significant members of an isotope group at a given p-value cut-off. For p<0.01 and p<0.0001, this returned 140 and 15 significant features, respectively, as shown in FIG. 5B. Next, tandem mass spectra were acquired for the 15 highly significant features, identifying four peptides from cyclin-dependent kinase 2, CDK2, two peptides from glycogen synthase kinase alpha subunit, GSKA3, and one peptide from Huntingtin-interacting protein K, HYPK, as shown in FIG. 5C. Annotated MS/MS identification spectra can be found in FIGS. 6A-G.

Identification of DPP3 as a Novel Target of Mdivi-1

Mdivi-1 is a small molecule member of a class of thioxodihydroquinazolinones that exhibits robust killing of a wide range of tumor cells including in cisplatin resistant ovarian cancers cells from patients who are refractory to cisplatin treatment cells.[22-24] Mdivi-1 has a molecular weight of 353.22 and has the following chemical structure:

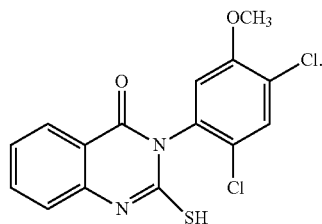 [SMILES: COc1cc(-n2c(S)nc3ccccc3c2=O)c(Cl)cc1Cl]

Equal aliquots of a2780cis cells were treated with 20 µM mdivi-1 and DMSO respectively, split into six technical replicates per condition, and heated to 56° C. for ten minutes to stimulate differential agglutination of drug-bound and unbound proteins. All samples were processed as described in the staurosporine experiment, and CHORUS was used to create and export a data cube that contained 522,600 aligned features in 218,388 isotope groups. Data-dependent MS/MS data was analyzed and results in the identification of 35,369 features linked to 5488 unique peptides sequences that were associated with 947 proteins. Features (184,801) having non-zero intensity values in at least four of six samples per condition were selected, and a Student's t-test was applied to compute a p value for each feature, and a volcano plot was created to show the distribution of features as a function of fold change and significance, as shown in the volcano plot in FIG. 7A. Features with two or more isotopes passing a p-value cut-off of 0.01 (270) and 0.001 (8) were selected and shown in FIG. 7B. Two of the significant features were identified as peptide VLLEAGEGLVTITPTTGSDGRPDAR (SEQ ID NO: 2) deriving from dipeptidyl peptidase 3, DPP3, using MS/MS spectra acquired during the initial dMS experiment. The 6 remaining highly significant features were identified as peptides EVDGEGKPYYEVR (SEQ ID NO: 6), EGITTYFSGNCTMEDAK (SEQ ID NO: 4), and GPSEAPSGQA (SEQ ID NO: 1) that are specific to the protein sequence for DPP3, using MS/MS spectra acquired in subsequent analyses. In total, eight DPP3 peptides from 18 features were significant in the analysis, and intensity plots across samples are shown in FIG. 7C; the annotated MS/MS spectra that confirmed the identification of the DPP3 peptides are found in FIGS. 8A-G. Only a single peptide derived from DPP3, VILGSEAAQQHPEEVR (SEQ ID NO: 7), did not show a significant intensity change in the mdivi-1 treated samples.

The observation that DPP3 function was inhibited by mdivi-1 suggests that DISRUPT provides a selective and unbiased approach for identifying and ranking novel drug targets without the use of a priori knowledge or protein identification.

Quantitative and Functional Confirmation of Mdivi-1/DPP 3 Interaction

Protein quantification by western blot was employed to confirm the relative abundance of DPP3 remaining in solution following treatment with mdivi-1, heating and centrifugation. Cytoplasmic lysates from a2780cis ovarian cancer cells were treated with 20 µM mdivi-1 of and heated to 44° C., 48° C., 52° C., 56° C., and 60° C., in singlicate; the western blot is shown in FIG. 9D. β-actin was used as a control blot to show an unchanging drop in intensity as a function of temperature. The samples treated with mdivi-1 remained in solution at 52° C. and 56° C. at higher levels compared to vehicle treated controls. The blot was also probed for DRP1 and showed no evidence of a thermal shift with mdivi-1 treatment. DPP3 activity was measured using a polypeptide cleavage assay that measures a decrease in fluorescence due to the removal of an n-terminal bound fluorophore. Fluorescence was measured as a function of dose, as shown in FIG. 9E; the control and quench assays for the functional assay are shown in FIG. 9D. DPP3 showed a significant reduction in activity when exposed to mdivi-1, with an estimated $IC_{50}$ of 70 nM.

Evaluation of Ranking and Sample Size by Iterative Cross-Validation

Figure 10:
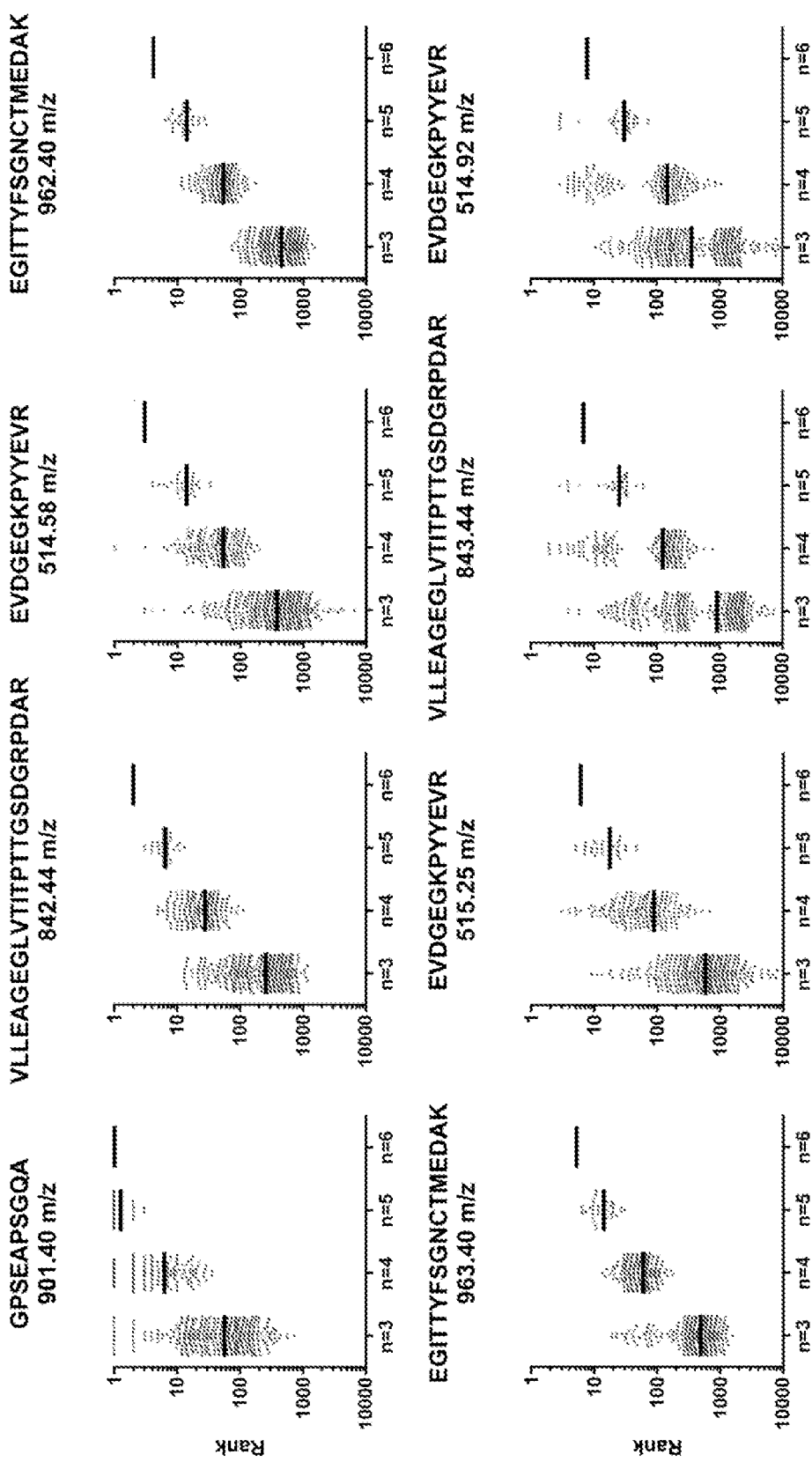
FIG. 10 is a graphical illustration of a cross validation demonstration of ranking improvement through greater sample number. Cross validation was performed using all possible combinations of samples to create unique n=3, n=4, and n=5 experiments from the original n=6 experiments resulting in 400, 225, and 36 iterations, respectively. The eight most significant features were identified through their peptide sequence and isotopic mass to charge ratio. All new rankings for the eight features were shown for the n=3, n=4, and n=5 cross validation experiments, demonstrating poorer ranking accuracy and precision with lower sample numbers.

To determine if sample size affects the ranking of putative protein targets, the data files (n=6 per condition) from the mdivi-1 experiment were combined into all possible groupings for n=3, n=4, and n=5 files per condition. This resulted in 400, 225, and 26 unique groupings, respectively, that were analyzed using identical filtering and statistical cut-offs as the original experiment that included six samples per condition. The eight most statistically significant features belonged to DPP3, as shown in the volcano plot in FIG. 5A and the scattered dot plots in FIG. 10. In the 400 experimental groupings that employed n=3 data files, the 8 most significant DPP3 features had a median statistical ranking of 341, with a $25^{th}$ to $75^{th}$ percentile range of 106 to 722.5. Grouping of n=4 samples per condition resulted in 225 combinations and a median ranking of 40, with a $25^{th}$ to $75^{th}$ percentile range of 16 to 88. The 36 possible combinations of n=5 data files resulted in a median statistical ranking of 12 with a $25^{th}$ to $75^{th}$ percentile range of 6 to 22. For comparison, analysis of the full data set returned a median rank of 4.5 for the eight most significant DPP3 features, with a $25^{th}$ to $75^{th}$ percentile range of 2.75 to 6.25.

Methods

A. Preparation of Cell Extracts for Using in CETSA Experiments

Adherent cultures of a2780cis cells (mdivi-1 experiments, obtained from Sigma Aldrich) or K562 cells (staurosporine experiments, obtained from ATCC, Manassas, Va.) were grown at 37° C. with 5% $CO_2$. Cells were harvested at a density of 2 to 3×10/\6 cells per mL and centrifuged at 300×g in 20 mL ice-cold phosphate-buffered saline (PBS) pH 7.4 to pellet cells. The cell pellet was resuspended in 5 mL ice-cold PBS (mdivi-1) or kinase buffer (25 mM Tris-HCl (pH 7.5), 5 mM b-glycerophosphate, 2 mM dithiothreitol, 0.1 mM Na3VO4, 10 mM MgCl2, for staurosporine experiments, catalog #9802 Cell Signaling Technologies, Boston Mass.), supplemented with protease inhibitors (Roche, Copenhagen, DE) and snap frozen in liquid nitrogen. The lysate stock was placed on ice until thawed. This freeze-thaw cycle was repeated twice, and the lysed contents were cleared of debris by centrifugation at 25,000×g for 20 min. Protein concentrations of the cleared lysate was determined spectrophotometrically using a 660 nm assay (Bio-Rad, Hercules, Calif.) and aliquots were snap frozen in liquid nitrogen and stored at −80° C.

B. Thermal Shift Assay Using Cell Extract

Stock solutions of 1 mM mdivi-1 and staurosporine were prepared in 100% dimethyl sulfoxide (DMSO). Mdivi-1 was added to the lysate to a final concentration of 20 µM, staurosporine was diluted in lysate to a final concentration of 2 µM, resulting in 0.02% and 0.002% DMSO respectively including matching DMSO vehicle controls. The extract was incubated with compound at room temperature for one hour. The extracts were then divided into 50 uL aliquots such that six (mdivi-1) and ten (staurosporine) replicates are prepared for both compound and vehicle treatment. Replicates were heated in parallel at their respective temperatures for 10 min, followed by a 5 minute incubation at room temp. Samples were then centrifuged at 25,000×g for 20 min at 4° C. and the supernatant transferred to a clean tube.

C. Sample Preparation for MS

Samples were denatured and digested utilizing the FASP method described by Wisniewski et al. (2009) and Manza et al. (2005). Briefly, cells were exchanged into 8 M urea and alkylated with 22.5 mM iodoacetamide in a 30 kDa Microcon Forensic Column (Millipore, Billerica, Mass.) across multiple 14,000×g centrifugations prior to exchange into 25 mM ammonium bicarbonate. Proteins were digested overnight using a 1:100 ratio of Mass Spectrometry Grade, TPCK-treated trypsin (Promega, Madison, Wis.) prior to collection into a new tube. Samples were desalted on C18 SPE columns as described previously.[26] Samples were concentrated in a vacuum dessicator prior to resuspension. Upon desiccation, samples were resuspended in 0.1% formic acid in water.

D. LC-MS/MS Analysis

The nanoLC-ESI-MS/MS analysis was performed on an UltiMate3000 nanoLC ((Dionex, Sunnydale, CA). 3 ug of tryptic peptides were injected into via autosampler onto a 25 cm×75 uM ID reversed phase column packed with 3 uM Reprosil (New Objective, Boston, MA) heated to 50° C. Peptides were separated and eluted on a gradient from 1% acetonitrile to 28% acetonitrile in 0.1% formic acid over 70 minutes at 300 nL/min. Samples were injected online into a Velos Pro mass spectrometer using a data-dependent top 5 method in positive mode, with spray voltage set at 1.9 kV. Full scan spectra were acquired in the range of m/z 350-1400 at 60,000 resolution using an automatic gain control target of 1e6, excluding charge states of +1. For each full MS scan, the top 5 most intense ions were fragmented using higher energy collision& dissociation at 32.5% normalized collision energy and an MSn ion target of 5e4, before being excluded for 60 seconds.

E. MS Data Processing

Raw files were uploaded to a cloud-based processing repository www.chorusproject.org (Infoclinka, Ukraine). All raw files are retention time and accurate mass-aligned, at the level of individual features within isotope envelopes using a proprietary alignment algorithm and searched against human reference protein database (Uniprot human ref 20150303.fasta via Comet) using a 10 parts per million peptide precursor mass tolerance. Carbamidomethylation of cysteine residues and oxidation of methionine were used as fixed modifications, and n-terminal acetylation was used as a variable modification.

F. Feature, Isotope Envelope, Peptide, and Protein Quantification

For MS peak detection a 2D raster image was formed where the X axis represented retention time (RT), Y axis was m/z, and the raster values represented instrument measurement values at the correspondent RT and m/z data points. After the image was formed from the raw LC/MS data, the general image processing methods were applied to separate real signals from noise, detect boundary of LC/MS peaks, detect monoisotopic m/z and charge of the isotope groups, and extract peak intensities.

G. Image Processing Steps

Local maximums were detected all over the image. Peaks were formed based on local maximum and its immediate surroundings. Background "snow" noise was filtered out. The criteria was the size of the peak being very small (1 pixel in RT). Remaining peaks were filtered using various criteria like shape and size. List of features were formed from good peaks. Cleaned and smoothed images were produced.

H. Isotope Grouping

Peaks were sorted on descending intensity and isotope groups were assembled starting from the highest peak. All possible charges were tried (1 to 7 typically) and any adjacent peaks were identified in appropriate locations (calculated based on charge and start rt and m/z). Isotope group candidate was validated using theoretical intensities distributions and the best was chosen.

I. Alignment Over all the Files in the Experiment

Figure 11:
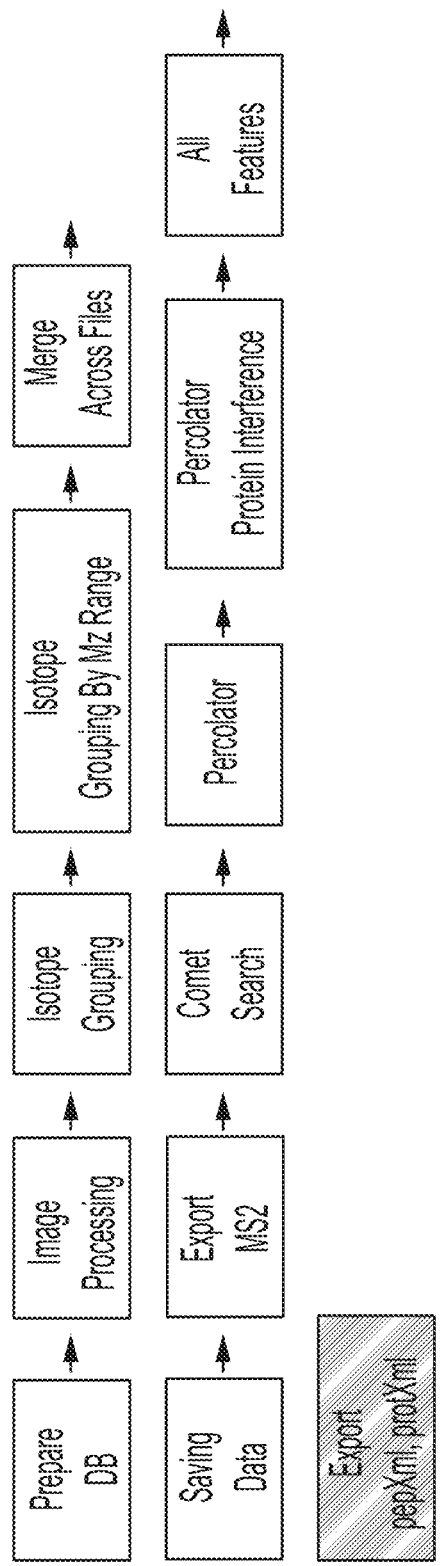
FIG. 11 is a schematic showing steps involved in the CHORUS cloud computing analytical workflow.

Most probable alignment RT shift was calculated for pairs of files; shift density distribution were built and for each RT, shifts that maximize the density were chosen. Files were aligned using the calculated RT shifts curve. Isotope group features correlations were used to match among files in the RT shift window. These steps are diagrammed in FIG. 11.

J. Statistical and Practical Filtering of Chorus Output

All features that were not present in at least two thirds of each of the vehicle and treatment groups were excluded. Following a two-tailed equal variance student's t-test, all features that did not belong to an isotope group with a minimum of two features with a $p<0.01$ were excluded. All remaining unidentified features were analyzed by targeted mass spectrometric analysis employing the same equipment and gradient as the original analysis. Feature m/z were selected for repetitive data dependent analysis over a determined length of time. MaxQuant was used to identify features, and features were matched by accurate mass, retention time, and MS/MS fragmentation scan using a false discovery rate of 1%.

K Western Blot Analysis

Lysates of A2780cis cells were prepared identically as DISRUPT experiments outlined above. The soluble protein was separated on Tris-glycine gels (Invitrogen). The separated proteins were blotted onto a polyvinylidene difluoride (PVDF) membrane and non-specific binding was blocked overnight at 4° C. in phosphate-buffered saline containing 0.1% Tween 20 and 10% nonfat dry milk (blocking buffer). Membranes were incubated with primary antibodies, DPP3 (GeneTex), Drpl (BD Biosciences), and β-actin (Sigma-Aldrich), in blocking buffer overnight at 4° C. Membranes were then washed and incubated in peroxidase conjugated anti-rabbit IgG (Sigma-Aldrich) or anti-mouse IgG (Sigma-Aldrich) secondary antibody for 1 h at room temperature. Membranes were developed using SuperSignal West Femto Maximum Sensitivity Substrate (Thermo Fisher Scientific).

L. DPP3 Activity Assay

The inhibition of DPP3 peptidase activity by mdivi-1 was evaluated using a commercially available fluorogenic DPP3 Assay Kit (catalog number 80203, BPS Bioscience, San Diego Calif.) that contains purified recombinant DPP3 protein and DPP3 substrate Arg2-AMC. The fluorescence intensity was measured using a microplate reader, Synergy 2 (BioTek instruments).

M Statistical Analysis of Effect of Sample Size on Rank Accuracy

Using the data from the n=6 mdivi-1 experiment, all unique combinations of n=3, n=4, and n=5 experiments were created without repetition, resulting in 400, 225, and 36 simulated experiments, respectively. Data was analyzed using a student's two tailed t-test and features ranked by statistical significance.

Discussion

Thermal stability assays, through the use of mass spectrometric or large scale antibody screening, have advanced to the point that a single experiment can profile thousands of proteins, offering a powerful tool for the investigation of novel drug-protein interactions and the development of new medicines[8]. Mass spectrometry alone allows for the investigation and quantification of large portions of the proteome without the need for specific antibodies; however, experimental designs and analytical approaches that efficiently discriminate true binding events from non-specific interactions. In addition, the discovery of novel interactions requires unbiased methods that do not depend on a priori knowledge of small molecule or target proteins.

Using the DISRUPT platform, known kinases that bind to the kinase inhibitor staurosporine were successfully ranked. Twelve of the most significant 15 features found following practical and statistical filtering belonged to known kinase interactors. The method also successfully identified a novel target for the putative cancer drug mdivi-1. Using a single temperature and multiple replicates, nine features out of 522,600 were ranked using statistical and practical filters as described. The eight most significant features were identified as peptides with amino acid sequence belonging to dipeptidyl peptidase 3 (DPP3). Orthogonal biochemical validation employing the published CETSA approach (western blot) and commercially available substrate turnover assay (fluorescent peptide) was used to confirm mdivi-1 binds to and functionally modulates the activity of DPP3. It is important to note that DPP3 expression is elevated in several gynecological cancers including ovarian.[25,26]

Without being bound by theory, the robust and accurate ranking of the DISRUPT method may be attributed to 1) the use of multiple technical replicates at a single temperature, and 2) the use of differential mass spectrometry that prioritizes the quantification high resolution full scan data over the identification of peptide by tandem mass spectrometry. An effective discovery platform or screening technology must be able to discriminate true positives from false positives. DISRUPT has a novel experimental design; rather than investigate samples in singlicate across a wide temperature range, we use greater sample sizes for heightened statistical sensitivity.

To demonstrate this effect, a cross validation experiment that examined the mdivi-1/DPP3 results using all possible subsets of data in groups of n=3, 4, 5, and 6 was performed. Reducing the number of samples per group resulted in poorer ranking accuracy and precision for the features that correspond to the putative target DPP3; to distinguish signal form noise, the number of samples used must be appropriately matched to the experimental variation (in this case n=6).

Moreover, the ranking accuracy of the DISRUPT method is a result of the emphasis that differential mass spectrometry places on high-resolution full scan data. The dMS approach does not rely on the acquisition of MS/MS spectra and obviates the need for newer hybrid instrumentation that emphasizes MS/MS scan speeds. It allows for identification of significant features following quantification and statistical analysis, providing true unbiased discovery of unknown proteins. Importantly, the methodology examines all data acquired by the mass spectrometer, not just the data associated with an MS/MS scan event. By doing so, the dynamic range of the experiment is defined by the dynamic range of the high-resolution mass spectrometer, in this case a hybrid orbital ion trap, not the limited range of identifiable features from data-dependent acquisition. As described by Michalski et al., only a small fraction of the more than 100,000 detectable isotope groups are accessible for selection and identification by data-dependent acquisition. By quantifying first and identifying later, the dMS workflow eliminates the burden of acquiring and searching large numbers of MS/MS spectra for proteins that do not show a significant change in relative abundance. The identification of significant features is a simple matter of acquiring MS/MS spectra for a far smaller number of specific features, after significance has been established. In addition, dMS interrogates all features independently; other methodologies rely on identification and combine features into peptides or proteins prior to quantification. Data analysis at the feature level is unbiased by identification accuracy and has the advantage that noisy and clean signals are not combined.

The DISRUPT methodology would not be possible without a scalable data analysis platform, such as CHORUS, that can quickly translate, align, and quantify a large amounts of high-resolution full-scan data and enable statistical processing and visualization of results. CHORUS data structures (datacubes) typically contain approximately 500,000 features and built-in statistical analysis tools can analyze all of this data and output the subset of statistically significant features. To test that CHORUS tools can accurately integrate features, a dMS analysis of a pooled sample was used to measure the coefficients of variation of features across a $10^4$ range of intensity matched those generated by manual integration.

The DISRUPT methodology may prove more difficult to implement than other thermal shift methodologies. The DISRUPT methodology places great importance on sample reproducibility in both preparation and analysis. Samples are run serially on the mass spectrometer, not in parallel as employed by Savitski et al; serial sample runs require very highly reproducible chromatography for Chorus to be able to align features accurately over multiple samples. In addition, since samples are not multiplexed, large multifactorial experiments can grow to take significant amounts of instrument time, although this is somewhat mitigated by the use of fewer temperatures than the CETSA method as currently described in the literature. Although multiple samples were used, no fractionation was employed to improve identification depth; new information about drug/protein binding was acquired in less than a week, a speed that would allow for integration into different stages of the drug discovery pipeline making it amenable to early and late stage investigation. The method proved powerful enough that employing a single temperature was able to identify known and novel protein binding targets successfully, but the method is robust enough to allow for multifactorial investigations that could employ differential temperature, dosing, and other chemical and physical factors. Looking forward, DISRUPT could easily adjust to include automation and scale into current drug discovery platforms[6]. It is a powerful tool to reexamine current drugs with unclear or unknown modes of action or adverse effects caused by unknown off target proteins.

IV. References

1. Drews, J. Drug discovery: a historical perspective. Science 287, 1960-4 (2000).
2. Jafari, R. et al. The cellular thermal shift assay for evaluating drug target interactions in cells. Nat Protoc 9, 2100-22 (2014).
3. Lomenick, B. et al. Target identification using drug affinity responsive target stability (DARTS). Proc Natl Acad Sci USA 106, 21984-9 (2009).
4. Minde, D. P., Maurice, M. M. & Rudiger, S. G. Determining biophysical protein stability in lysates by a fast proteolysis assay, FASTpp. PLoS One 7, e46147 (2012).
5. Kell, D. B., Dobson, P. D., Bilsland, E. & Oliver, S. G. The promiscuous binding of pharmaceutical drugs and their transporter-mediated uptake into cells: what we (need to) know and how we can do so. Drug Discov Today 18, 218-39 (2013).
6. Stern, A. M., Schurdak, M. E., Bahar, I., Berg, J. M. & Taylor, D. L. A Perspective on Implementing a Quantitative Systems Pharmacology Platform for Drug Discovery and the Advancement of Personalized Medicine. J Biomol Screen 21, 521-34 (2016).
7. Lee, J. A., Uhlik, M. T., Moxham, C. M., Tomandl, D. & Sall, D. J. Modern phenotypic drug discovery is a viable, neoclassic pharma strategy. J Med Chem 55, 4527-38 (2012).
8. Pantoliano, M. W. et al. High-density miniaturized thermal shift assays as a general strategy for drug discovery. J Biomol Screen 6, 429-40 (2001).
9. Weber, P. C. & Salemme, F. R. Applications of calorimetric methods to drug discovery and the study of protein interactions. Curr Opin Struct Biol 13, 115-21 (2003).
10. Broach, J. R. & Thorner, J. High-throughput screening for drug discovery. Nature 384, 14-6 (1996).
11. Carnero, A. High throughput screening in drug discovery. Clin Transl Oncol 8, 482-90 (2006).
12. Lavinder, J. J., Hari, S. B., Sullivan, B. J. & Magliery, T. J. High-throughput thermal scanning: a general, rapid dye-binding thermal shift screen for protein engineering. J Am Chem Soc 131, 3794-5 (2009).
13. Pai, M. Y. et al. Drug affinity responsive target stability (DARTS) for small-molecule target identification. Methods Mol Biol 1263, 287-98 (2015).
14. Almqvist, H. et al. CETSA screening identifies known and novel thymidylate synthase inhibitors and slow intracellular activation of 5-fluorouracil. Nat Commun 7, 11040 (2016).
15. Jensen, A. J., Martinez Molina, D. & Lundback, T. CETSA: a target engagement assay with potential to transform drug discovery. Future Med Chem 7, 975-8 (2015).
16. Savitski, M. M. et al. Tracking cancer drugs in living cells by thermal profiling of the proteome. Science 346, 1255784 (2014).
17. Reinhard, F. B. et al. Thermal proteome profiling monitors ligand interactions with cellular membrane proteins. Nat Methods 12, 1129-31 (2015).
18. Michalski, A., Cox, J. & Mann, M. More than 100,000 detectable peptide species elute in single shotgun proteomics runs but the majority is inaccessible to data-dependent LC-MS/MS. J Proteome Res 10, 1785-93 (2011).
19. Zhao, X. et al. Differential mass spectrometry of rat plasma reveals proteins that are responsive to 17beta-estradiol and a selective estrogen receptor modulator PPT. J Proteome Res 7, 4373-83 (2008).
20. Wiener, M. C., Sachs, J. R., Deyanova, E. G. & Yates, N. A. Differential mass spectrometry: a label-free LC-MS method for finding significant differences in complex peptide and protein mixtures. Anal Chem 76, 6085-96 (2004).
21. Meng, F. et al. Quantitative analysis of complex peptide mixtures using FTMS and differential mass spectrometry. J Am Soc Mass Spectrom 18, 226-33 (2007).
22. Qian, W. et al. The combination of thioxodihydroquinazolinones and platinum drugs reverses platinum resistance in tumor cells by inducing mitochondrial apoptosis independent of Bax and Bak. Bioorg Med Chem Lett 25, 856-63 (2015).

23. Wang, J. et al. A novel strategy for targeted killing of tumor cells: Induction of multipolar acentrosomal mitotic spindles with a quinazolinone derivative mdivi-1. *Mol Oncol* 9, 488-502 (2015).
24. Qian, W. et al. Novel combination of mitochondrial division inhibitor 1 (mdivi-1) and platinum agents produces synergistic pro-apoptotic effect in drug resistant tumor cells. *Oncotarget* 5, 4180-94 (2014).
25. Simaga, S., Babic, D., Osmak, M., Sprem, M. & Abramic, M. Tumor cytosol dipeptidyl peptidase III activity is increased with histological aggressiveness of ovarian primary carcinomas. *Gynecol Oncol* 91, 194-200 (2003).
26. Simaga, S. et al. Dipeptidyl peptidase III in malignant and non-malignant gynaecological tissue. *Eur J Cancer* 34, 399-405 (1998).

What is claimed is:

1. A method of identifying a protein capable of binding a ligand, the method comprising:
   (a) contacting the ligand with two or more samples comprising a plurality of proteins in a solution;
   (b) differentiating the proteins bound to the ligand ("bound proteins") from the proteins that are not bound to the ligand ("unbound proteins") in each sample;
   (c) denaturing and digesting the plurality of proteins to form a plurality of peptides in each sample;
   (d) quantifying a plurality of molecular features contained in the plurality of peptides in each sample, wherein the molecular features are defined as having a mass to charge ratio, retention time, and peak intensity as measured by mass spectrometry;
   (e) ranking the molecular features that exhibit a statistically significant difference in quantity between the samples contacted with the ligand and a sample that is not contacted with the ligand ("statistically significant molecular feature");
   (f) identifying one or more amino acid sequences of the statistically significant molecular features that are highly ranked; and
   (g) identifying a protein that comprises the amino acid sequences of step (f);
   wherein step (b) comprises titrating each sample with a solvent, solution, surfactant, detergent, or any combination thereof to solubilize or maintain the solubility of the bound proteins while the unbound proteins remain non-solubilized or precipitate out of solution, thereby differentiating the bound proteins from the unbound proteins.

2. The method of claim 1, wherein step (a) comprises solubilizing the proteins using a surfactant, a detergent, or any combination thereof.

3. The method of claim 2, wherein the detergent comprises octylglucyl pyranoside or dodecyl maltoside.

4. The method of claim 1, wherein each sample is titrated with acetone or methanol.

5. The method of claim 1, wherein after step (c) but prior to step (d) the plurality of peptides are analyzed using nano-scale liquid chromatographic tandem mass spectrometry.

6. The method of claim 1, wherein step (e) comprises using differential mass spectrometry.

7. The method of claim 6, further comprising assigning the molecular features to an isotope group characterized by a chemical formula and an isotope distribution.

8. The method of claim 1, wherein ranking the statistically significant molecular features comprises statistical and practical filtering.

9. The method of claim 8, wherein the statistically significant molecular features that are determined to still be significant based upon the statistical and practical filtering are highly ranked.

10. The method of claim 8, wherein the statistical filtering comprises t-tests.

11. The method of claim 8, wherein the practical filtering comprises excluding any statistically significant molecular features that are not present in at least two-thirds of the samples contacted with the ligand.

12. The method of claim 8, wherein the practical filtering comprises excluding any statistically significant molecular features that were the only significant features in a single isotope group with a p value of less than about 0.01 based on the statistical filtering.

13. The method of claim 1, wherein step (e) comprises CHORUS web application for storing, sharing, visualizing, and analyzing spectrometry files.

14. The method of claim 1, wherein step (g) comprises comparing the amino acid sequences of the statistically significant molecular features with a protein database and identifying which proteins of the protein database contain the statistically significant molecular features.

15. The method of claim 1, wherein the solvent, solution, surfactant, detergent, or any combination thereof is a solution to lower the dielectric constant such that the solubility of the bound protein is different in the sample contacted with the ligand than the solubility of that same protein in a sample not contacted with the ligand.

* * * * *